(12) United States Patent
Perez et al.

(10) Patent No.: US 7,498,481 B2
(45) Date of Patent: Mar. 3, 2009

(54) METHOD FOR OBTAINING A MONOCOTYLEDON PLANT CONTAINING A GENE OF INTEREST FREE OF FOREIGN ANCILLARY SEQUENCE

(75) Inventors: Pascual Perez, Chanonat (FR); Denise Gerentes, Le Crest (FR); Sebastien Praud, Royat (FR)

(73) Assignee: Biogemma, Paris (FR)

( * ) Notice: Subject to any disclaimer, the term of this patent is extended or adjusted under 35 U.S.C. 154(b) by 534 days.

(21) Appl. No.: 10/733,080

(22) Filed: Dec. 11, 2003

(65) Prior Publication Data

US 2004/0199938 A1    Oct. 7, 2004

Related U.S. Application Data

(63) Continuation of application No. PCT/FR02/01656, filed on May 16, 2002.

(30) Foreign Application Priority Data

Nov. 7, 2001    (FR) .................................. 01 07597

(51) Int. Cl.
C12N 15/82    (2006.01)
C12N 15/87    (2006.01)
C12N 15/09    (2006.01)
C12N 15/63    (2006.01)
A01H 1/00    (2006.01)

(52) U.S. Cl. .................... 800/278; 800/260; 800/320.1; 800/291; 435/468

(58) Field of Classification Search ........................ None
See application file for complete search history.

(56) References Cited

U.S. PATENT DOCUMENTS

2002/0157129 A1* 10/2002 Perez et al. .................. 800/278

FOREIGN PATENT DOCUMENTS

| WO | 9201370 | 2/1992 |
| WO | WO 92/01370 | * 2/1992 |
| WO | 9741228 | 11/1997 |
| WO | 9838323 | 9/1998 |
| WO | WO 98/38323 | * 9/1998 |
| WO | WO01/07632 | 2/2001 |

OTHER PUBLICATIONS

Bennetzen (Plant Molecular Biology, 42:251-269, 2000).*
Ishida et al. (Nature Biotechnology, 14(6):745-750, 1996).*
Dellaporta et al. (Molecular cloning of the maize R-nj allele by transposon tagging with Ac, pp. 263-282, in Chromosome structure and function: Impact of new concepts, edited by J.P. Gustafson and R. Appels, Plenum Press, New York).*
Yoshida et al. (Journal of Bioscience and Bioengineering, 90:353-362, 2000).*
Negrotto et al. (2000) "The use of phosphomannose-isomerase as a selectable marker to recover transgenic maize plants (Zea mays L.) via Agrobacterium transformation", Plant Cell Receptors 19: 798-803.
Chesson et al. (2000) "Qui a peur des OGM", Le Recherche 327: 26-44.
Chopra et al. (1999) "Molecular characterization of a mutable pigmentation phenotype and isolation of the first active transposable element from Sorghum bicolor", PNAS 96: 15330-15335.
Nielsen et al. (1999) "A transient expression system to assay putative antifungal genes on powdery mildew infected barley leaves", Physiological and Molecular Plant Pathology 54: 1-12.
Grotewold et al. (1998) "Engineering secondary metabolism in maize cells by ectopic expression of transcription factors", The Plant Cell 10: 721-740.
Grotewold et al. (1998) "Engineering secondary metabolism in maize cells by ectopic expression of transcription factors", The Plant Cell 10: 721-740.
Luetke et al. (1997) "Asymmetry in Flp-mediated cleavage", Nucleic Acids Research 25: 4240-4249.
Motohashi et al. (1996) "Identification of Tnr3, a suppressor-mutator/enhancer-like transposable element from rice", Mol. Gen. Genet. 250: 148-152.

(Continued)

*Primary Examiner*—Phuong T Bui
*Assistant Examiner*—Vinod Kumar
(74) *Attorney, Agent, or Firm*—Baker Botts L.L.P.

(57) ABSTRACT

The present invention relates to a method for obtaining a transgenic monocotyledon plant containing a gene of interest free of foreign ancillary sequences comprising:

a) transforming at least one cell of a plant having no active transposase with a vector comprising two expression cassettes, one comprising a nucleotide sequence of interest (i), the other comprising a nucleotide sequence encoding a selection marker (ii) bordered by the mobilizable sequences of a transposon, said first expression cassette (comprising the nucleotide sequence of interest (i)) being outside the transposon element;

b) selecting the transformed plants with the selection marker (ii);

c) crossing a transformed plant with another plant belonging to a line containing in its genome a gene encoding an endogenous active transposase, and which is in the middle of a phenotypic marker for excision (iii), to obtain an F1 or any other individual of a subsequent generation;

d) selecting the cells or the individuals carrying the gene of interest free of foreign ancillary sequence, from the F1 generation;

e) regenerating plants from the cells or the individuals selected in (d).

9 Claims, 7 Drawing Sheets

OTHER PUBLICATIONS

Ishida et al. (1996) "High efficiency transformation of maize (*Zea mays* L.) mediated by *Agrobacterium tumefaciens*", Nature Biotechnology 14: 745-750.
Bodeau et al. (1994) "Anthocyanin genotypes in an A188 background, and their pigment phenotypes in embryogenic calli", MNL 68: 98-99.
Yoder et al. (1994) "Transformation systems for generating marker-free transgenic plants", Bio/Technology 12: 263-267.
Chalfie et al. (1994) "Green fluorescent protein as a marker for gene expression", Science 263: 802-805.
MacRae et al. (1994) "Molecular evolutionary characterization of an Activator (Ac)-like transposable element sequence from pearl millet (*Pennisetum glaucum*) (Poaceae)", Genetica 92: 77-89.
Bechtold et al. (1993) "In planta Agrobacterium mediated gene transfer by infiltration of adult *Arabidopsis thalian* plants", Molecular Biology and Genetics 316: 1194-1199.
Manninen et al. (1993) "BARE-1, a copia-like retroelement in barely (*Hordeum vulgare* L.)" Plant Molecular Biology 22: 829-846.
Hood et al. (1993) "New Agrobacterium helper plasmids for gene transfer to plants", Transgenic Research 2: 208-218.
Finer et al. (1992) "Development of the particle inflow gun for DNA delivery to plant cells", Plant Cell Reports 11: 323-328.
Depigny-This et al. (1992) "The cruciferin gene family in radish", Plant Molecular Biology 20: 467-479.
Flavell et al. (1992) "Selectable marker genes: safe for plants?", Bio/Technology 10: 141-144.
Lazo et al. (1991) "A DNA transformation-competent arabidopsis genomic library in Agrobacterium", Bio/Technology 9: 963-967.
McElroy et al. (1991) "Construction of expression vectors based on the rice actin 1 (Act1) 5' region for use in monocot transformation", Mol. Gen. Genet. 231: 150-160.
Fromm et al. (1990) "Inheritance and expression of chimeric genes in the progeny of transgenic maize plants", Bio/Technology 8: 833-839.
White et al. (1989) "A cassette containing the bar gene of *Streptomyces hygroscopicus*: a selectable marker for plant transformation", Nucleic Acids Research 18: 1062.
Ludwig et al. (1989) "Lc, a member of the maize R gene family responsible for tissue-specific anthocyanin production, encodes a protein similar to transcriptional activators and contains the myc-homology region", Proc. Natl. Acad. USA 86: 7092-7096.
Robert et al. (1989) "Tissue-specific expression of a wheat high molecular weight glutenin gene in transgenic tobacco", The Plant Cell 1: 569-578.
Chupeau et al. (1989) "Transgenic plants of lettuce (*Lactuca sativa*) obtained throough electroporation of protoplasts", Bio/Technology 7: 503-508.
Anderson et al. (1989) "The characterization and comparative analysis of high-molecular-weight glutenin genes from genomes A and B of a hexaploid bread wheat", Theor. Appl. Genet. 77: 689-700.
Lechelt et al. (1989) "Isolation and molecular analysis of the maize P locus", Mol. Gen. Genet. 219: 225-234.
Dellaporta et al. (1988) "Molecular cloning of the maize R-nj allele by transposon tagging with Ac", Plenum Press: 263-282.

Hartley, R.W. (1988) "Barnase and Barstar. Expression of its cloned inhibitor permits expression of a cloned ribonuclease", J. Mol. Biol. 202: 913-915.
Guerche et al. (1987) "Genetic transformation of oilseed rape (*Brassica napus*) by the Ri T-DNA of *Agrobacterium rhizogenes* and analysis of inheritance of the transformed phenotype", Mol. Gen. Genet. 206: 382-386.
Neuhaus et al. (1987) "Transgenic rapeseed plants obtained by the microinjection of DNA into microscope-derived embryoids", Theor. Appl. Genet. 75: 30-36.
Kay et al. (1987) "Duplication of CaMV 35S promoter sequences creates a strong enchancer for plant genes", Science 236: 1299-1302.
Richard A. Jefferson (1987) "Assaying chimeric genes in plants: the GUS gene fusion system", Plant Molecular Biology Reporter 5: 387-405.
Hood et al. (1986) "The hypervirulence of *Agrobacterium tumefaciens* A281 is encoded in a region ofpTiBo542 of T-DNA", Journal of Bacteriology 168: 1291-1301.
Schocher et al. (1986) "Co-transformation of unlinked foreign genes into plants by direct gene transfer", Bio/Technology 4: 1093-1096.
An Gynheung (1986) "Development of plant promoter expression vectors and their use for analysis of differential activity of nopaline synthase promoter in transformed tobacco cells", Plant Physiol. 81: 86-91.
Pereira et al. (1986) "Molecular analysis of the En/Spm transposable element system of *Zea mays*", The EMBO Journa.
Armstrong et al. (1985) "Establishment and maintenance of friable, embryogenic maize callus and the involvement of $_L$-proline", Planta 164: 207-214.
Rosen et al. (1983) "An unusual transposon encoding heat shock inducible and developmentally regulated transcripts in dictyostelium", Cell 35: 243-251.
Herrera-Estella et al. (1983) "Chimeric genes as dominant selectable markers in plant cells", The EMBO Journal 2: 987-995.
Bevan et al. (1983) "Structure and transcription of the nopaline synthase gene region of T-DNA", Nucleic Acids Research 11: 369-385.
Ooms et al. (1982) "Studies on the structure of cointegrates between octopine and nopaline Ti-plasmids and their tumour-inducing properties", Plant Molecular Biology 1: 265-276.
Depicker et al. (1982) "Nopaline synthase: transcript mapping and DNA sequence", Journal of Molecular and Applied Genetics 1: 561-573.
Franck et al. (1980) "Nucleotide sequence of cauliflower mosaic virus DNA", Cell 21: 285-294.
Brink et al. (1973) "Mutable R-navajo alleles of cyclic origin in maize", Genetics 73: 273-296.
MaizeGDB: Maize Genetics Nomenclature "A Standard For Maize Genetics Nomenclature." (1995).
Walker, et al. "Insertions of a Novel Class of Transposable Elements With a Strong Target Site Preference at the *r* locuus of Maize" Genetics 146: 681-693; Jun. 1997.
Li, et al. "Gene Conversion Within Regulatory Sequences Generates Maize *r* Alleles With Altered Gene Expression." Genetics 159: 1727-1740; Dec. 2001.

* cited by examiner

Insertion of a sequence containing the
DS::NptII element between the RB and LB borders of pSB12

Insertion of a sequence containing the
DS::*bar* element between the RB and LB borders of pSB12

SEQUENCE LISTING

<160> NUMBER OF SEQ ID NOS: 8

<210> SEQ ID NO 1
<211> LENGTH: 20
<212> TYPE: DNA
<213> ORGANISM: Artificial sequence
<220> FEATURE:
<223> OTHER INFORMATION: Artificial sequence description:
      synthetic oligonucleotide

<400> SEQUENCE: 1
cgacaatctg atcatgagcg                                          20

<210> SEQ ID NO 2
<211> LENGTH: 21
<212> TYPE: DNA
<213> ORGANISM: Artificial sequence
<220> FEATURE:
<223> OTHER INFORMATION: Artificial sequence description:
      synthetic oligonucleotide

<400> SEQUENCE: 2
cttaataaca cattgcggac g                                        21

<210> SEQ ID NO 3
<211> LENGTH: 18
<212> TYPE: DNA
<213> ORGANISM: Artificial sequence
<220> FEATURE:
<223> OTHER INFORMATION: Artificial sequence description:
      Synthetic oligonucleotide

<400> SEQUENCE: 3
cgaattcgcg ccggtaac                                            18

<210> SEQ ID NO 4
<211> LENGTH: 23
<212> TYPE: DNA
<213> ORGANISM: Artificial sequence
<220> FEATURE:
<223> OTHER INFORMATION: Artificial sequence description:
      Synthetic oligonucleotide

<400> SEQUENCE: 4
tcgtgccgaa ttcgatatca agc                                      23

<210> SEQ ID NO 5
<211> LENGTH: 25
<212> TYPE: DNA
<213> ORGANISM: Artificial sequence
<220> FEATURE:
<223> OTHER INFORMATION: Artificial sequence description:
      Synthetic oligonucleotide EM11

<400> SEQUENCE: 5
cattgcggac gttttaatg tactg                                     25

<210> SEQ ID NO 6
<211> LENGTH: 21
<212> TYPE: DNA
<213> ORGANISM: Artificial sequence
<220> FEATURE:
<223> OTHER INFORMATION: Artificial sequence description:
      Synthetic oligonucleotide Barn5

<400> SEQUENCE: 6

```
ggtttcgctc atgtgttgag c                                              21

<210> SEQ ID NO 7
<211> LENGTH: 985
<212> TYPE: DNA
<213> ORGANISM: Arabidopsis thaliana

<400> SEQUENCE: 7
ctcgaggtcg acggtatcga taagcttgca tgcctgcagg tagacattgt aggttggttt     60
tgatgatgat aagtaatcat tggagaattg tctaacacat gcactggaga attattgact   120
ctaccacgtt ctctttgata ttcctcgatt ttcctcgtga tttcatcagc ctctccgaaa   180
aagtaattgt atccactaga actttgggaa tctcccatct aatttatgta ttagagaagt   240
tataatattt tggggaaata gattttctct actgattttg ttgtgtgaca ttatattttt   300
ataagtacat gtttctgttt cgttatattg ttgtcgtggt tgagtcttta ttagagcatg   360
taaatatgtt tatgaaataa gcgagaaagg aattaattaa acgtatcgag tgataaatgc   420
tttaatggat tcgagattta gtattcttaa attttgttt cattatcatt gattataaaa    480
ctaagttatg ttgatctcaa atccttaatt atgttctcct aagaagagta caagtggtgg   540
gaacgaaaga tgagtaaaat actaaaaatc ttttctcaaa agtcaaatcg cattagttaa   600
caaaaacaaa ccatgtgtta ccgtcaaatc aatgtgttta aagatgtta accactaatc     660 aagcatttac gtgtaaccgg atcaaccgga tttgggtttt gaatatgttg tggagatgta   720
tataaatgat aaattaattg aatatcttaa ttaatctgtg aaagaaacta catcacacac    780
tttgttattt cccctagctt ttagtttttt tatcatgcaa aacttatgaa gtaactagat   840
caagatcaca aaaaaaaagc atcacttcac ttcatgacct aattattctc gaagcccaaa   900
actatttaca tacactttta ttctataaat atagatgatg gaattcacca atccaaaagt    960
gaataaaaaa cacaagtact ctaga                                          985

<210> SEQ ID NO 8
<211> LENGTH: 898
<212> TYPE: DNA
<213> ORGANISM: Bacillus amyloliquefaciens

<400> SEQUENCE: 8
aagcttctag accatggcac aggttatcaa cacgtttgac ggggttgcgg attatcttca     60
gacatatcat aagctacctg ataattacat tacaaaatca gaagcacaag ccctcggctg    120
ggtggcatca aagggaacc ttgcagacgt cgctccgggg aaaagcatcg gcggagacat     180
cttctcaaac agggaaggca aactcccggg caaaagcgga cgaacatggc gtgaagcgga    240
tattaactat acatcaggct tcagaaattc agaccggatt ctttactcaa gcgactggct    300
gatttacaaa acaacggacc attatcagac ctttacaaaa atcagataac gaaaaaaacg    360
gcttcctgcg gaggccgttt ttttcagctt tacataaagt gtgtaataaa ttttttcttca    420 aactctgatc ggtcaatttc actttccgga tccggtccaa tctgcagccg tccgagacag    480
gaggacatcg tccagctgaa accggggcag aatccggcca tttctgaaga gaaaaatggt    540
aaactgatag aataaaatca taagaaagga gccgcacatg aaaaaagcag tcattaacgg    600
ggaacaaatc agaagtatca gcgacctcca ccagacattg aaaaaggagc ttgcccttcc    660
ggaatactac ggtgaaaacc tggacgcttt atgggattgt ctgaccggat gggtggagta    720
cccgctcgtt ttggaatgga ggcagttga acaaagcaag cagctgactg aaaatggcgc    780
```

-continued

```
cgagagtgtg cttcaggttt tccgtgaagc gaaagcggaa ggctgcgaca tcaccatcat    840
actttcttaa tacgatcaat gggagatgaa caatatggaa acacaaaccc gcaagctt     898
```

METHOD FOR OBTAINING A MONOCOTYLEDON PLANT CONTAINING A GENE OF INTEREST FREE OF FOREIGN ANCILLARY SEQUENCE

This application is a continuation of International Patent application No. PCT/FR02/01656 filed May 16, 2002 and published in French as WO 02/101061 on Dec. 19, 2002, which claims priority to French Patent Application No. FR 01/07597 filed Jun. 11, 2001.

BACKGROUND OF THE INVENTION

The present invention relates to a method for obtaining a monocotyledon plant containing a gene of interest free of foreign ancillary sequence.

Plant transgenesis comprises introducing into a plant one or more genes originating from various organisms (bacteria, viruses, insects, plants), with the aim of providing it with novel characteristics and of improving certain agronomic or dietary qualities. The great diversity of genes, combined with the development of conventional techniques for genetic transformation, has resulted in the creation of novel plant varieties. In some cases, farming practices can be facilitated and yields increased by virtue of the introduction of characteristics which confer resistance to a herbicide, to pathogens or to various forms of stress. In other cases, the nutritive value of the plant and the content of certain essential compounds can be enhanced. However, the integration of genes into a genome during a process of transgenesis occurs with very low frequency. For this reason, in most cases, either a selection marker gene, which gives a selective advantage to the transformed cells, or a phenotypic marker, which allows those skilled in the art to identify the transformed cells among the others is genetically linked to the genes of interest.

Selection marker genes, such as genes for resistance to antibiotics or to herbicides, are essential for detecting the transformation events. However, they remain in the plant and, consequently, can also be detected in the form of DNA or of proteins in certain derived products, whereas generally they do not provide any added value to the transformed plant obtained. The presence of these genes, and in particular the genes for resistance to antibiotics and herbicides, is today at the center of numerous debates regarding genetically modified organisms (Flavell et al., 1992; Chesson et al., 2000).

It is therefore necessary to develop systems which make it possible to eliminate these selection genes, once the transformants have been isolated by virtue of the selective agent and/or by molecular analyses. Several more or less complex methods of elimination have been studied, such as:

cotransformation, which consists in introducing two T-DNAs (transfer DNAs) into the organism, the first with the gene of interest and the other with the selection gene. This method is used rather for species with a short reproductive cycle. Transformants carrying the transgene of interest but having lost the selection gene are then selected in the descendants by segregation;

systems which exploit recombination at specific sites, such as the cre/lox system of the P1 bacteriophage or the yeast FLP/FRT system (FliPase recombinase; Lyzrik et al., 1997) used for species with a long reproductive cycle (maize, shrubs); however, these systems remain complex and laborious;

elimination systems which exploit the properties of mobile genes present in many genomes, such as retroelements and transposons, and in particular the maize Ac/Ds system used in many species.

Transposable elements in general, including in particular the Ac/Ds system, can excise themselves and reinsert into the genome during cell development. These elements may also not find a recipient site into which they can insert themselves, and are then degraded by nucleases. Transposons are mainly used for cloning and tagging certain genes with visible expression phenotypes (Dellaporta et al., 1988), but they can also be used to mobilize, excise and eliminate genes (PCT/US91/04679).

A system using maize Ac/Ds and allowing the elimination of selection marker genes in the tomato, a species which does not naturally possess any Ac or Ds element, has been described by Yoder et al. (1993).

However, this system, which has been tried and tested in heterologous plants of the dicotyledon type (tomato, garden arabis, tobacco), appeared, up until now, difficult to exploit in monocotyledons, in particular maize, a species in which Ac/Ds is naturally present. Specifically, the presence of endogenous elements makes it difficult to control and exploit this system.

SUMMARY OF THE INVENTION

In the context of the present application, the inventors have succeeded in developing a new original method for eliminating marker genes in monocotyledons, in particular in maize, using a system of endogenous transposons, such as, for example, the Ac/Ds system.

A subject of the present invention is therefore a method for obtaining a transgenic monocotyledon plant containing a gene of interest (i) free of foreign ancillary sequence comprising:

a) transforming at least one cell of a plant having no active transposase with a vector comprising two expression cassettes, one comprising a nucleotide sequence of interest (i), the other comprising a nucleotide sequence encoding a selection marker (ii) bordered by the mobilizable sequences of a transposon, said first expression cassette (comprising the nucleotide sequence of interest (i)) being outside the transposon element;

b) selecting the transformed plants with the selection marker (ii);

c) crossing a transformed plant with another plant belonging to a line containing in its genome a gene encoding an endogenous active transposase, and which is in the middle of a phenotypic marker for excision (iii), to obtain an F1 or any other individual of a subsequent generation;

d) selecting the cells or the individuals carrying the gene of interest free of foreign ancillary sequence, from the F1 generation;

e) regenerating plants from the cells or the individuals selected in (d).

The invention also provides host cells and plant transformation vectors. In some embodiments of the invention, a vector of the invention may comprise:

a first expression cassette comprising a nucleotide sequence of interest (i) not operably linked to mobilizable sequences of a transposon; and a second expression cassette comprising a nucleotide sequence encoding a selection marker (ii) operably linked to the mobilizable sequences of a transposon, wherein said nucleotide sequence encoding a selection marker (ii) is operably linked to a plant expression control sequence.

DETAILED DESCRIPTION OF THE INVENTION

Figure 1:
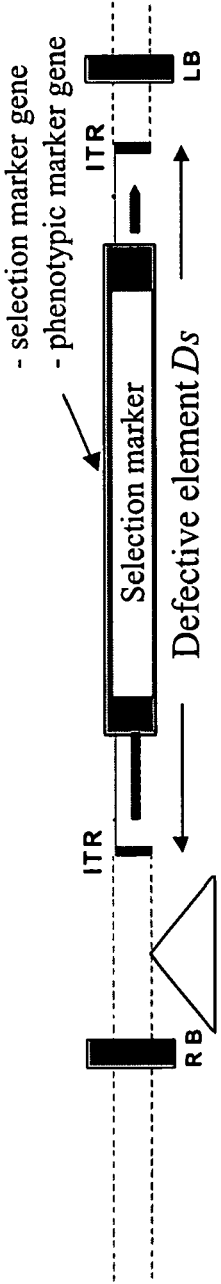
FIG. 1: Scheme of the two components of the system: Ds::M to be eliminated and the source of transposase.
Figure 1:
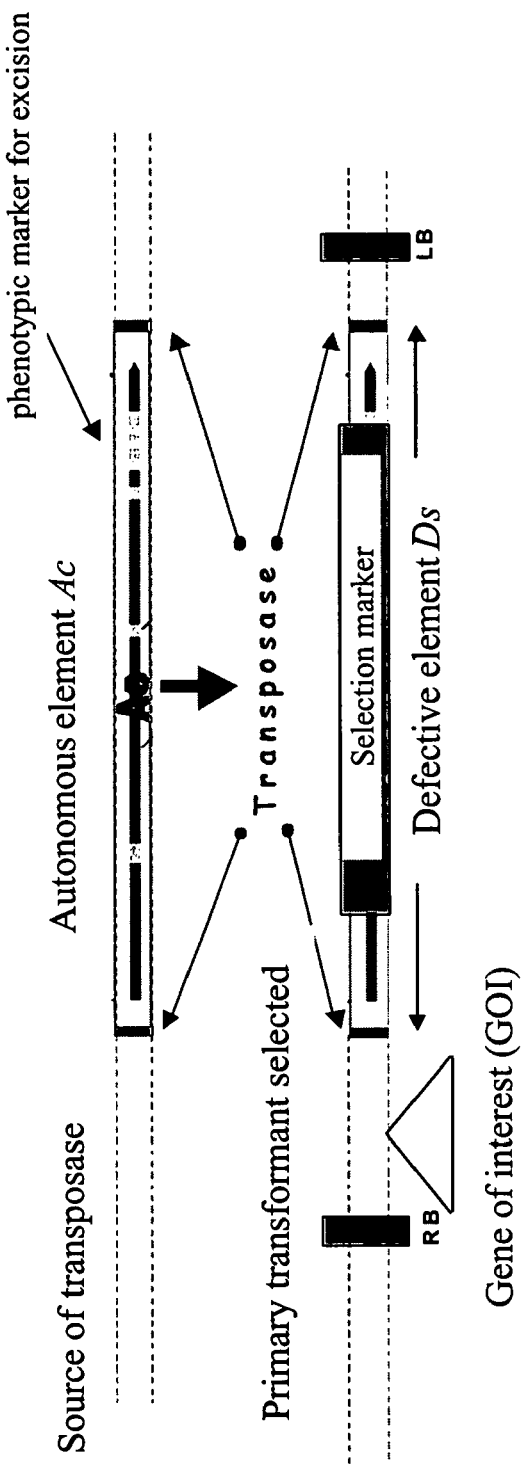
Figure 2:
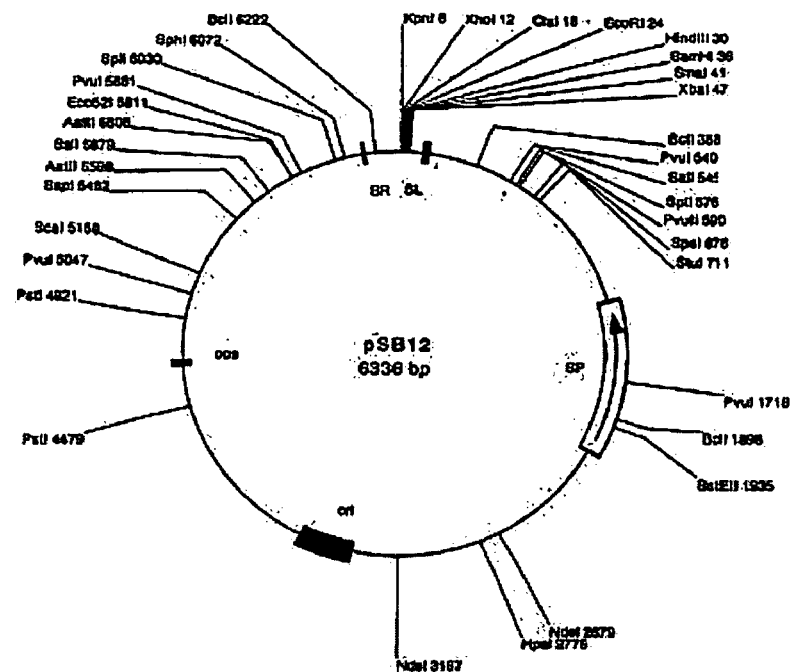
FIG. 2: Restriction maps of the plasmids pBios340-nptII (FIG. 2A) and pBios342-bar (FIG. 2B), derived from the plasmid pSB12.
Figure 2:
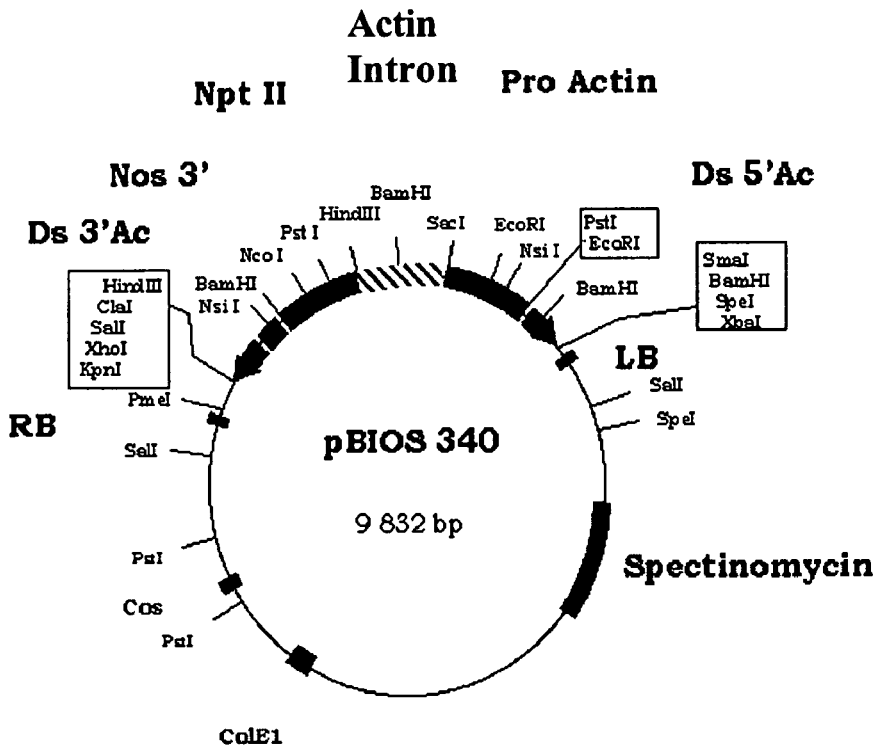
Figure 2:
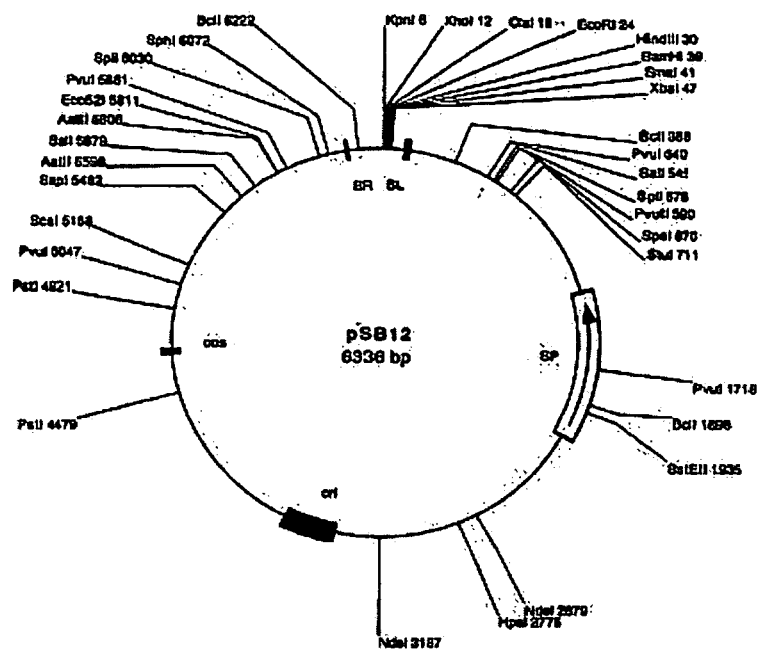
Figure 2:
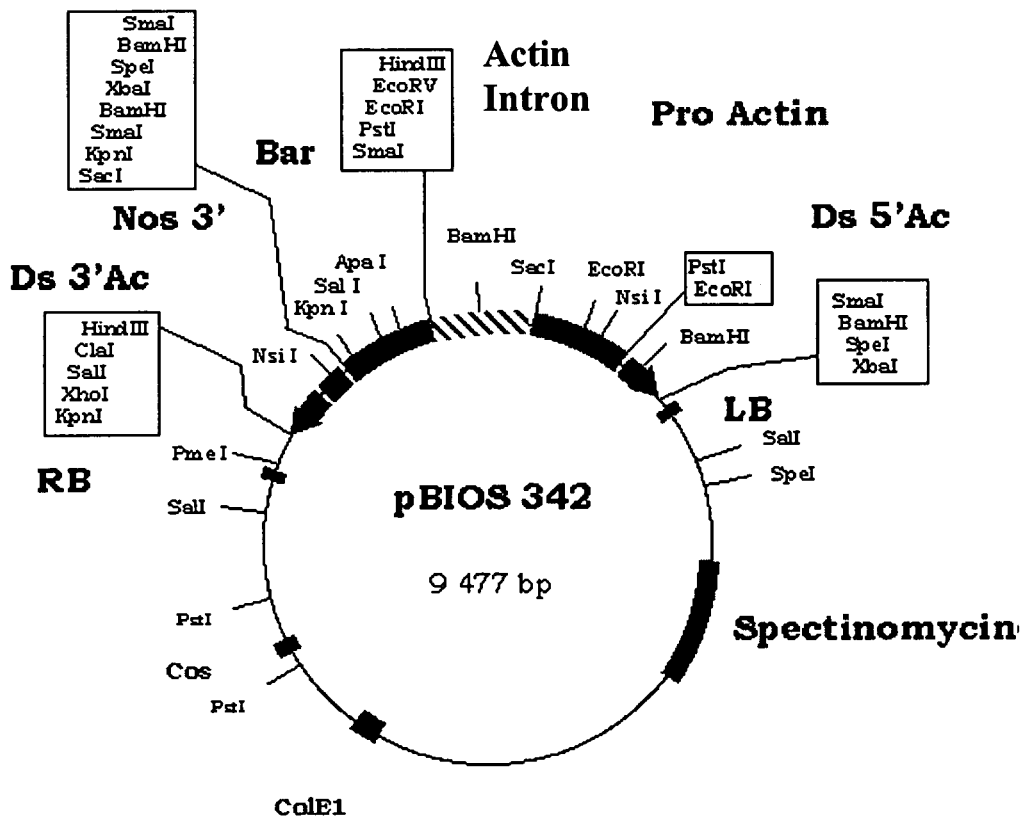
Figure 3:
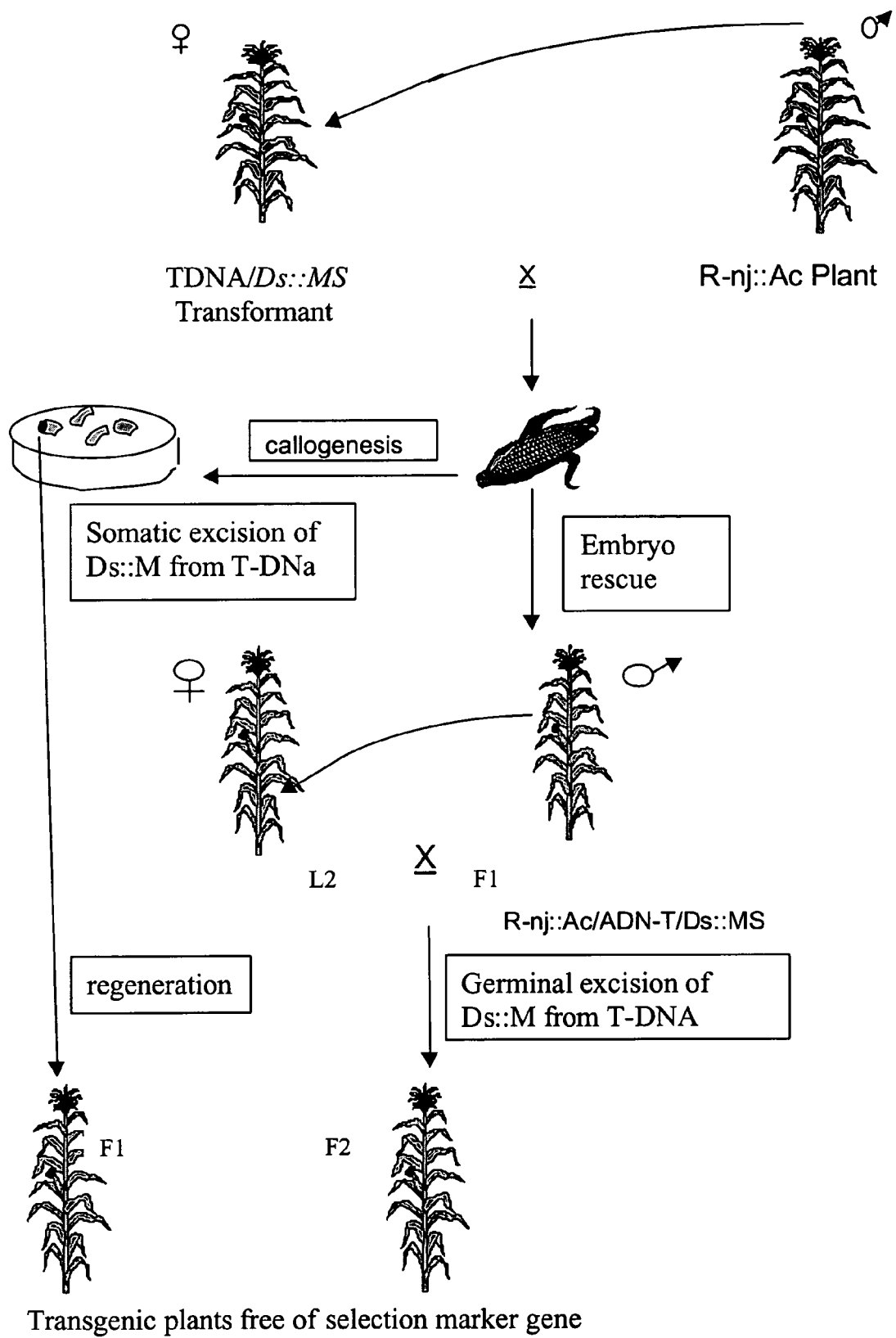
FIG. 3: Scheme of the two possible pathways for obtaining transgenic plants free of selection marker gene.
Figure 4:
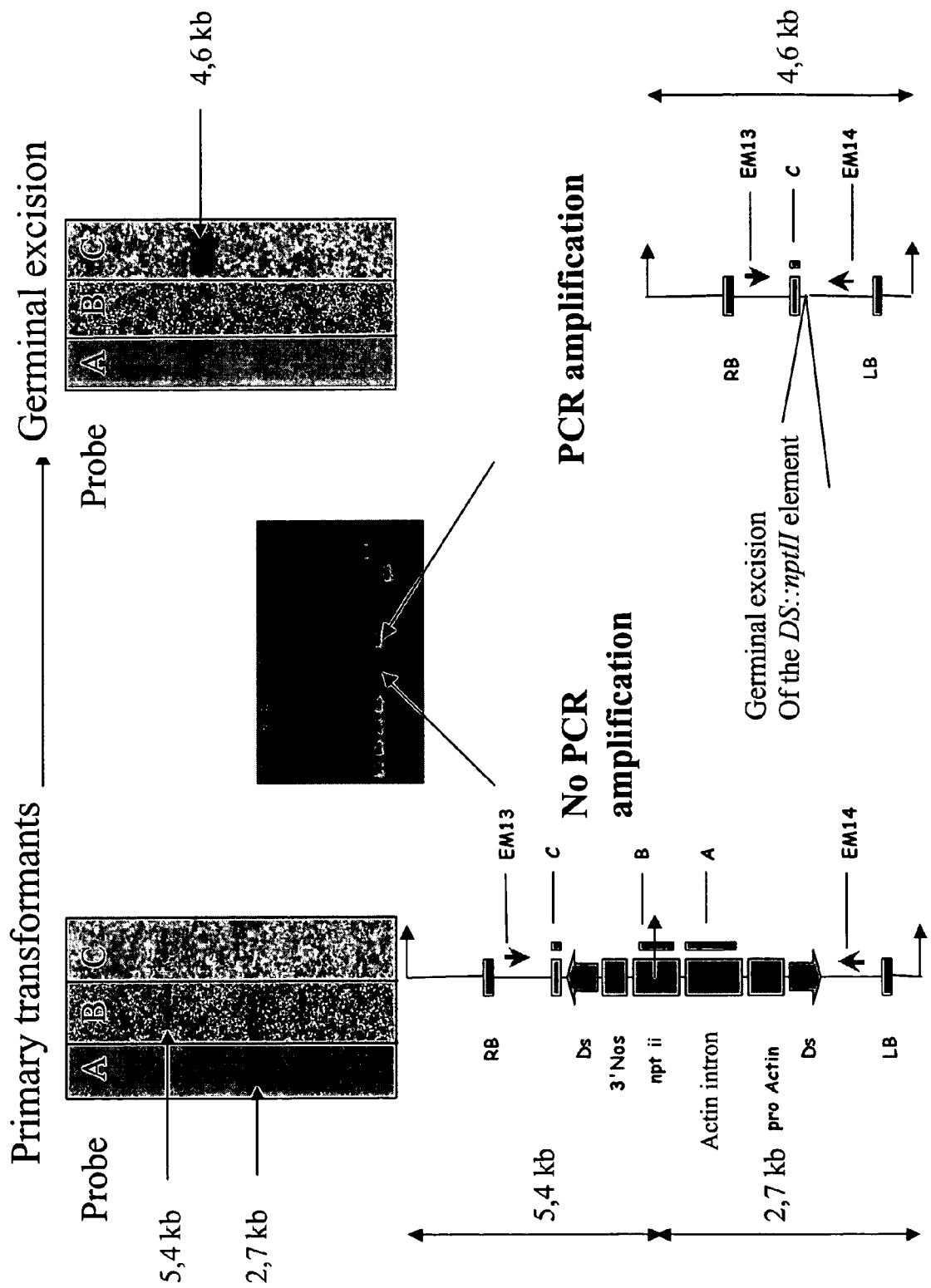
FIG. 4: observation of the germinal excision
Figure 5:
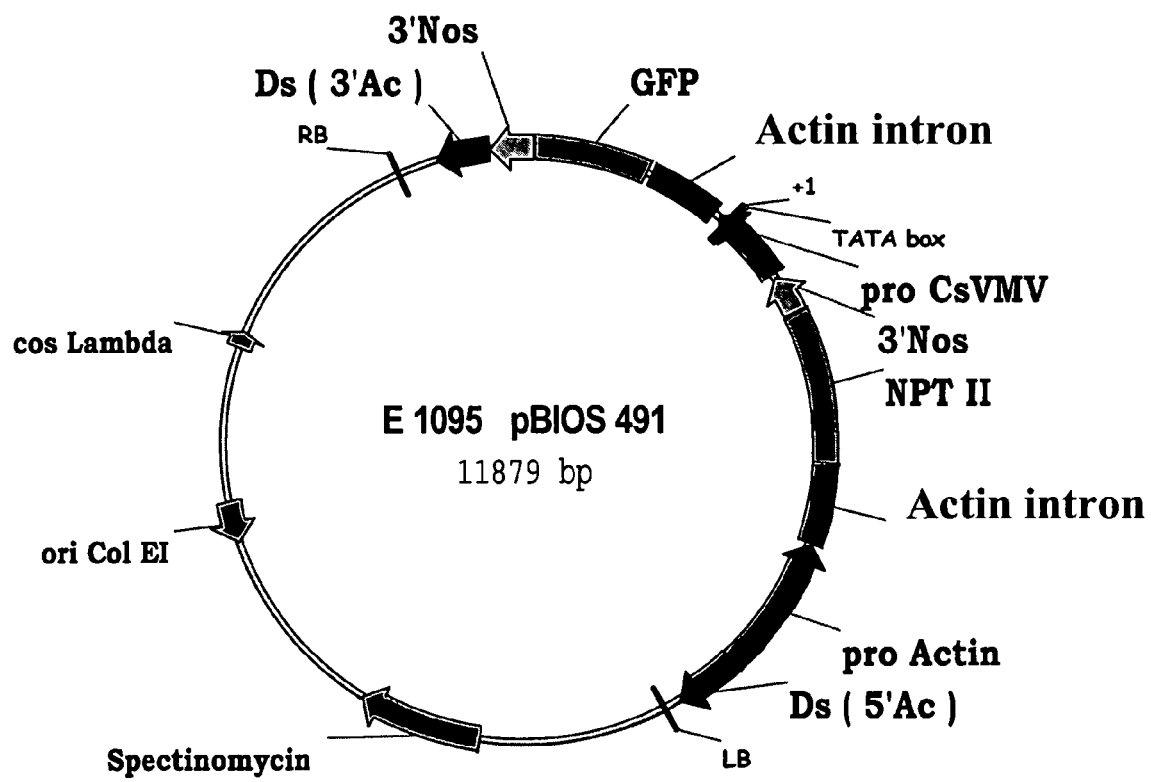
FIG. 5: restriction map of the plasmid pBios491 comprising the GFP gene and the NptII gene in a Ds element.

The term "foreign ancillary sequences" means sequences (ii) encoding a selection marker which may also be a phenotypic marker for selecting a transfected plant from a plant which does not contain the transfected foreign DNA. In some embodiments of the present invention, a selection marker sequence or selection marker gene is a gene which confers resistance to an antibiotic (Herrera-Estrella et al., 1983), or resistance to a herbicide (EP 242 246). For example, the selection marker may be selected from the group consisting of:

- the sul gene which confers resistance to the sulfonamide herbicide Asulam (WO 98/49316),
- the nptII gene which confers resistance to kanamycin (Bevan et al., 1983),
- the hph gene which confers resistance to hygromycin (Herrera-Estrella et al., 1983),
- the bar gene which confers tolerance to bialaphos (White et al., 1990),
- the EPSPS gene which confers tolerance to glyphosate (U.S. Pat. No. 5,188,642),
- the HPPD gene which confers tolerance to isoxazoles (WO 96/38567), and
- the chloramphenicol acetyltransferase (CAT) gene which detoxifies chloramphenicol.

In the context of the invention, the bar gene or the nptII gene will preferably be used.

In some embodiments of the present invention, a phenotypic marker or phenotypic marker gene, useful as a selection marker (ii) in the method according to the invention, may be a reporter gene which allows selection via a phenotypic, colorimetric or luminescent criterion and which is readily detectable, For example, the phenotypic marker gene may be selected from the group consisting of:

- the gene encoding the β-glucuronidase (GUS) enzyme (Jefferson et al., 1987),
- the gene encoding the green fluorescent protein, GFP, which makes it possible to visualize the transformed cells under UV (Chalfie et al., 1994), and also all the other GFP-derived fluorescent proteins, and
- the nptII gene which, when used at low dose, inhibits chloroplast synthesis In addition, the phenotypic marker gene may be any gene which allows the expression of a pigment such as, for example, the genes involved in the synthesis of flavonoids (anthocyans, phlobaphenes and derivatives), which can be used as reporter genes in cereal transformation. This reporter system allows the expression of pigments ranging from red to violet in certain transformed tissues. Flavonoid synthesis genes may be selected from the group consisting of the Lc (Ludwig et al., 1990), B and C1 regulatory genes involved in the synthesis of anthocyans and the P gene involved in the synthesis of phlobaphenes (Grotewold et al., 1998).

According to a preferred embodiment, it is possible to integrate into the expression cassette comprising a nucleotide sequence encoding a selection marker (ii) another phenotypic marker gene of the type such as a reporter gene with nondestructive selection, so as to facilitate the selection steps by simple nondestructive visual observation. Nondestructive selection markers may be selected from the group consisting of Green Fluorescent Protein (GFP) described by Nielsen et al. (1999) and any other variant of GFP which can be used in plants, such as, for example, those described by Seth J. Davis (1998).

A tissue-specific or organ-specific promoter may be operably linked to the phenotypic marker gene (ii) to differentiate expression of the phenotypic marker gene (ii) and the phenotypic marker for excision (iii).

The present invention therefore relates to a system with two components, which are represented in FIG. No. 1:

- a first plant which has no active transposase although it exhibits an endogenous transposon system, into which a construct, comprising the expression cassette for the gene of interest (i) and that for the selection marker gene (ii), can be integrated; and
- a second plant containing in its genome a gene encoding an endogenous active transposase, and which is inserted into a phenotypic marker for excision (iii).

Preferably, the monocotyledon plant transformed according to the invention contains no active transposase although it has an endogenous transposon system. Preferably, the transformed monocotyledon plant may be a maize plant, and it may belong to:

- the A188 line which contains no active transposase,
- an M1 line with no active transposase, derived from crossing the A188 and B73 lines, and favorable to the formation of highly regenerative type II calluses, or
- more generally, any other line containing no active transposase.

Transposable elements according to the invention may be selected from transposon families demonstrated in monocotyledons, such as:

- the Dotted (Dt) element, demonstrated in maize;
- the Mutator like (Mu) element family, demonstrated in maize and rice;
- the Activator/Dissociation like (Ac/Ds) family, demonstrated in maize (Müller-Neumann et al., 1984), barley (Chemyshev et al., 1988) and millet (MacRae et al., 1994);
- the CACTA like family, demonstrated in maize (Pereira et al., 1986), sorghum (Chopra et al., 1999), barley (Chemyshev et al., 1988) and rice (R. Mototashi et al., 1996);
- the copia like family, demonstrated in barley (Mannimem et al., 1993).

According to a preferred embodiment of the invention, the system for eliminating marker genes is the maize Ac/Ds system.

The elements of the Activator/Dissociation (Ac/Ds) family belong to the type II transposable elements, and are thus mainly made up of two domains:

- a gene which encodes the protein required for copy mobility, the transposase,
- two inverted terminal repeat ends called ITRs (Inverted Terminal Repeats). The ITRs and certain flanking sequences appear to serve as reference points for directing the action of the transposase.

The Ds element is an Ac element which has undergone considerable mutations or deletions in the sequence encoding the transposase. It can only become excised from its insertion site in the presence of an active transposase source Ac. It is therefore Ac-dependent.

By extension, a Ds element may be referred to as any element made up of two ITRs surrounding any internal sequence the size of which is less than that of the autonomous element.

According to the present invention, the DNA construct used in step (a) comprises an expression cassette for the gene of interest (i) and an expression cassette for the selection marker gene (ii).

The marker gene to be eliminated (ii) is integrated between two borders originating from the ends of an Ac element and containing the sequences required for transposition. The complete construct is inserted into the T-DNA which thus carries a Ds-type defective transposon element containing the selection gene. This element is called Ds::M (M for selection Marker or phenotypic Marker).

The gene of interest is on the T-DNA and outside the Ds::M transposable element.

According to the present invention, the nucleotide sequences of interest (i) may be any nucleic acid sequences which make it possible to introduce or improve an advantageous characteristic in the resulting transgenic plant. For example, the nucleic acid sequence may encode proteins or antisense RNA transcripts which may make it possible to improve nutritional values, the yield, the resistance to pathogens, to diseases, to drought, etc. Non-limiting examples of such genes are described in patent applications WO 91/02071 and WO 95/06128.

The nucleic acid sequences of interest may also be introduced as a genetic tool for generating mutants and/or assisting with the identification, molecular labeling or isolation of plant gene segments. Other examples are described in Weising et al., 1995.

According to the present invention, the nucleic acid of interest (i) is inserted into a nucleic acid construct, called an expression cassette for the gene of interest, and is operably linked to expression control sequences which allow it to be expressed and, optionally, to be regulated.

Expression control sequences may be selected from the group consisting of transcription promoters, activators, terminators, and combinations thereof. Promoters may be selected from the group consisting of constitutive promoters, tissue-specific or organ-specific promoters, and development-specific promoters.

In preferred embodiments, a constitutive promoter is used. Constitutive promoters may be selected from the group consisting of:
- the pAct 1 promoter of the rice Act 1 gene contained in the plasmid pAct1-F4 (Mc Elroy et al., 1991);
- the p35S promoter (Kay et al., 1987);
- a tissue-specific promoter, such as the wheat or barley HMWG promoter; and
- the pCRU promoter of the radish cruciferin gene.

The p35S promoter, the HMWG promoter, and the pCRU promoter all allow expression of the protein of interest in the seeds (Roberts et al., 1989; Anderson O. D. et al., 1989; Depigny-This et al., 1992).

Other elements, such as introns, enhancers, polyadenylation sequences and derivatives, may also be present in the nucleic acid sequence of interest, so as to improve the expression or the function of the transforming gene.

Advantageously, the expression cassette may also contain 5' untranslated sequences, referred to as 'leader' sequences. Such sequences can improve translation.

A terminator which may be used in the constructs of the invention, is the Nos terminator corresponding to the 3' non-coding region of the nopaline synthase gene of the *Agrobacterium tumefaciens* Ti plasmid (Depicker et al., 1982).

The expression cassette for the gene of interest (i) is inserted into a nucleotide vector, such as a plasmid, which also comprises the expression cassette for the marker gene (ii) inserted between two ITRs.

According to the present invention, the expression cassette for the marker gene (ii) comprises the nucleic acid encoding the selection marker or the phenotypic marker, flanked by the sequences required for its expression, in particular the transcription promoters, activators and terminators, as described above.

According to one embodiment of the method of the invention, the plant cells are transformed with a vector as defined above, which is transferred into a cellular host capable of infecting said plant cells by allowing the integration, into the genome of the cells, of the nucleotide sequences of interest initially contained in the genome of the above-mentioned vector. Advantageously, the cellular host used is a bacterial strain, such as *Agrobacterium tumefaciens*, in particular according to the method described in the article by An et al. (1986), or else *Agrobacterium rhizogenes*, in particular according to the method described in the article by Guerche et al. (1987).

For example, the plant cells can be transformed by transferring the T region of the tumor-indicating extrachromosomal circular plasmid Ti of *Agrobacterium tumefaciens*, using a binary system (Watson et al., 1994). To do this, two vectors are constructed. In one of these vectors, the T region has been removed by deletion, except for the left and right borders, a marker gene being inserted between them so as to allow selection in the plant cells. The other partner of the binary system is an auxiliary Ti plasmid, which is a modified plasmid no longer having a T region, but which still contains the vir virulence genes required to transform the plant cell.

According to a preferred embodiment, the method described by Ishida et al. (1996) may be used to transform the monocotyledons.

Other embodiments of the method of the invention may also be mentioned, in particular the methods for the direct transfer of genes into the plant cells, such as direct microinjection into plant embryoids (Neuhaus et al., 1987), infiltration in planta of inflorescences (Bechtold et al., 1993) or electroporation of protoplasts (Chupeau et al., 1989), or else direct precipitation of protoplasts using PEG (Schocher et al., 1986) or bombardment of calluses or of embryos using a gun with particles coated with the plasmid DNA of interest (Fromm M. et al., 1990).

According to another protocol, the transformation is carried out according to the method described by Finer et al. (1992), using a particle gun with tungsten or advantageously gold particles, on calluses or embryos.

The selection, in step (b), of the transformed plant cells may be carried out on selective medium or by simple visual observation when a phenotypic marker gene is used.

The crossing in step (c) is carried out between the transformed plant and another plant, having an endogenous active transposase which is in the middle of a phenotypic marker for excision (iii), so as to obtain an F1 or any other individual of a subsequent generation, according to the techniques known to those skilled in the art. The other plant is preferably an elite line with agronomic characteristics of interest.

According to the present invention, the expression "endogenous active transposase" means an active transposase obtained nontransgenically.

According to the present invention, the transformed and identified plant is crossed, in step (c), with another plant belonging to a line containing in its genome a gene encoding an endogenous active transposase, and which is inserted into a phenotypic marker for excision (iii).

Transposons have a tendency to become methylated over generations, in particular in maize, and their transcript is then no longer detectable. The active phase of the transposon therefore corresponds to a low state of methylation which allows normal transcription of the gene. By associating with the transposon a phenotypic marker for excision, it is possible to visualize the cells in which transposition has occurred and to quantify the level of activity of the transposon in the organism and thus visualize the production of transposase. The transposon is generally inserted between the promoter and the coding portion of the phenotypic marker for excision, making its expression impossible. When the transposon expresses the transposase, it can excise itself from the gene into which it was inserted, which restores the activity of the gene. It is thus possible to visualize, by phenotypic analysis, the cells in which there has been production of the transposase capable of excising the Ds::M element.

The expression "phenotypic marker for excision" (iii) means any gene encoding a pigment or any other gene making it possible to follow the evolution of excision of the Ac element. Without limitation, a phenotypic marker for excision may be any gene for which a mutation gives a visible phenotype on the seed or the plant or a part of the plant, for example genes involved in the biochemical pathway of anthocyans or of phlobaphenes. Mention may be made of the constitutive genes A1, A2, C2, Bz1 or Bz2 and the regulatory genes C1, Vp1, P1, P1 and R1. According to the present invention, the preferential allele may be the R-nj allele, which is an endogenous phenotypic marker of the R1 family present in certain maize lines. The allele R-nj::transposon carries an active Ac element, the chromosomal region to which R-nj belongs being particularly hypomethylated (Brink et al., 1973). When the Ac transposes outside the R-nj gene, the latter becomes generally functional again, which results in the production of violet anthocyan-containing sectors of the "navajo" type visible on the crown of the seed, including the embryo. This variegated phenotype is a good means for evaluating and localizing events for which there has been production of transposase. In addition, it makes it possible to verify the activity of the transposon over the generations, and to follow the transposase in the course of the crosses.

Examples of lines which may be used in step (c), containing in their genome a gene encoding an endogenous active transposase, which is inserted into a phenotypic marker for excision, include:

W22/R-nj::Ac, a line homozygous for the allele R-nj::Ac derived from seeds originating from the Stock Center;

A188/R-nj::Ac, a line homozygous for the allele R-nj::Ac introgressed into the A188 genetic background;

HiII/R-nj::Ac, a line homozygous for the allele R-nj::Ac introgressed into the Hill genetic background;

W23/P-vv, a line homozygous for the allele P-w derived from seeds originating from the Stock Center (an Ac element is inserted into the allele P-rr);

or, more generally, any line having an active transposon inserted into a gene with a visible phenotype and having the genotype required for its expression.

The allele carrying the Ac element, although unstable, can be transferred to other lines by several crosses. It is sufficient to verify, before the introgression, that the recipient line indeed has all the alleles required for the expression of the phenotype. In the case of the allele R-nj::Ac, the alleles A1, A2, Bz1, Bz2 and C1 should be present or can be introgressed.

The selection, in step (d), of the individuals which carry the gene of interest (i) free of foreign ancillary sequence can be carried out on F1 plants or F2 plants, or calluses derived from F1 embryos. The selection of the individuals can be performed by techniques known to those skilled in the art, such as PCR and Southern techniques, or techniques for phenotypic observations. Thus, it is possible to identify the transformed plants having a genomically-integrated T-DNA carrying the selection marker gene (ii), particularly transformed plants having a single of the integrated selection marker gene (ii). In addition, resistant F1 plants may be selected to search for somatic excisions, and sensitive F2 plants may be analyzed to detect possible germinal excisions.

The present invention also relates to a method for obtaining a transgenic monocotyledon plant containing a gene of interest free of foreign ancillary sequence, in which the selection, in step (d), of the individuals is carried out via the reproductive pathway and comprises the following steps:

selecting variegated F1 seeds;

selecting F1 plants displaying somatic excision of the Ds::M element, by a PCR technique;

selecting F1 plants displaying germinal excision of the Ds::M element, by a PCR technique;

obtaining F2 plants by sowing based on these events.

Thus, according to the present invention, the selection of the individuals carrying the gene of interest (i) free of foreign ancillary sequence may be derived from an analysis of the variegation of the transposon excision marker allele, on the F1 ears.

The present invention also provides a method for obtaining a transgenic monocotyledon plant containing a gene of interest (i) free of foreign ancillary sequence, in which the selection of the individuals, in step (d), is carried out via the vegetative pathway and comprises the following steps:

producing calluses from immature F1 embryos, visually selecting the calluses containing the T-DNA and the Ds::M element, multiplying calluses and searching for sectors of excision of the Ds::M element, and regenerating F1 plants from these sectors of excision.

According to the present invention, F1 plants can be obtained directly by regeneration from calluses selected in step (d), by in vitro culturing of immature embryos of F1 ears.

A subject of the invention is also transgenic monocotyledon plants or parts of plants, such as cells or calluses, containing a gene of interest free of ancillary sequences and capable of being obtained by one of the methods described above.

The hybrid monocotyledon plants, characterized in that they are obtained by crossing the plants obtained by the methods described above, are also part of the invention.

The invention relates in particular to maize plants.

The invention also comprises a method for selecting, in calluses, the cells exhibiting an excision of the Ds::M element for obtaining transgenic plants containing a gene of interest (i) free of foreign ancillary sequence, comprising the steps:

producing calluses from immature F1 embryos, visually selecting the calluses containing the T-DNA and the Ds::M element, multiplying calluses and searching for sectors of excision of the Ds::M element, regenerating F1 plants from these sectors of excision.

Callus formation is due to cell proliferation, i.e. a mass of undifferentiated and juvenilized cells which may give rise to bipolar embryos. The bipolar embryos may, under certain conditions known to those skilled in the art, behave like zygotic embryos—derived from fertilization between a female sex cell and a male sex cell—and produce a plant.

During the cell divisions which take place during the growth of the callus, a certain number of Ds::M transposon excision events will take place. The callus thus formed is therefore chimeric and contains sectors of cells having Ds::M and sectors of cells no longer having Ds::M.

The phenotypic marker gene makes it possible to identify the cells transformed during processes of transgenesis which have a phenotype which can be expressed in the callus.

Alternatively, this method may also be used to recognize the cells in which the phenotypic marker gene (iii) is no longer expressed, either due to extinction of the gene, or due to excision of the gene. A phenotypic marker gene of the type such as GFP or anthocyans or any other marker gene with colorimetric expression will preferably be chosen. The nptII gene, which inhibits chloroplast synthesis, may also be used.

The invention also relates to a vector comprising two expression cassettes as described above.

The invention also provides a host cell comprising a vector as defined above.

A subject of the invention is also a plant cell, or a clone of such a cell, transformed with a vector as described above.

The present invention may also be applied to other plants, in particular monocotyledons, which have:

a transposon system as described above, and a phenotypic marker system; for example of the anthocyan type, found in the Poaceae (maize, sorghum, wheat, oats, rice), which are the two essential components of the method according to the invention.

Among the monocotyledons which can also be obtained according to the same protocol, mention may be made, for example, of: *Sorghum bicolor*(sorghum), *Hordeum vulgare* (barley), *Triticum eastivum* (wheat), *Oriza sativa* (rice), *Pennisetum glaucum* (millet).

EXAMPLES

Example 1

Production of an Ac Inactive, A188 Line Stably Transformed with the Ds::M Element 1.1. Preparation of the Ds::M Constructs The Ac element, the sequence of which was used to prepare the Ds::M constructs, is the Ac inserted into the p locus (Lechelt et al., 1989) identical to Ac9 of the waxy gene (Fedoroff et al. 1983).

The ends of the Ds::M were then constructed by internal deletions of the Ac. Their sizes are:

337 bp for the 3' Ac end, and 404 bp for the 5' Ac end.

The example proposed in this invention relates to two vectors which exhibit a polylinker in a DNA construct, thus making it possible to introduce a gene of interest by cloning.

The plant transformations were carried out with two vectors, pBios340 and pBios342, described below, derived from the same starting vector pSB12 (Japan Tobacco, EP 672 752), containing the two borders LB and RB.

A selection marker gene (MS) was introduced into the Ds element, under the control of the rice actin 1 gene promoter followed by the rice actin first intron (Mc Elroy et al., 1991).

a) Ds::npt II (pBios340)

The plasmid pBios340 contains a T-DNA consisting of the borders of pSB12, the 5' end of the Ac element, the promoter and the first intron of the rice actin 1 gene, the nptII open reading frame (Bevan et al., 1983), the Nos terminator (of the gene which encodes nopaline synthase, isolated from *Agrobacterium tumefaciens*) and the 3' end of the Ac element.

Ds::npt II is 3428 bp in size (FIG. No. 2).

b) Ds::bar (pBios342)

The plasmid pBios342 has the same organisation as pBios340 and possesses the bar open reading frame (White et al., 1990) in place of the npt II open reading frame (FIG. No. 2).

Ds::bar is 3173 bp in size.

In the interests of simplicity, the expression cassette promoter-actin intron-npt II or bar open reading frame-Nos terminator will be considered as a functional npt II or bar gene.

1.2 Transformation of Maize and Regeneration a) Choice of a Line Having no Active Transposase Ac The lines which can be used should preferably contain no active transposase, in order for the T-DNA to be stable in the transformed plant, and should have a good capacity for transformation with *Agrobacterium tumefaciens*.

The A188 line is thus used, which is a line of the species *Zea mays* subsp mays.

In order to evaluate the activity of the endogenous transposases, the methylation state of the Ac elements is analyzed.

The DNA of each plant was digested with the BglII and PvuII endonucleases, separately, and then with a mixture of these two enzymes.

PvuII is a methylation-sensitive enzyme. Once the cytosine residue of its specific cleavage site is methylated (5'-C-A-G-$^m$C-T-G-3'), the enzyme can no longer cleave the sequence. This enzyme makes it possible to reveal a state of methylation of the sequence. It has only two cleavage sites in the sequence of the Ac element, which both belong to two regions rich in CpG dinucleotides. These islands are sensitive to methylation in plants. The PvuII-PvuII fragment of Ac is 2524 bp in size.

BglII is an endonuclease which has no site within the Ac element, but which is quite common in the maize genome.

The genomic DNA digestion products were separated by agarose gel electrophoresis and transferred onto nylon membranes.

A 1605 bp probe, SAc, was obtained by digestion of the Ac element with the HindIII endonuclease. This HindIII-HindIII fragment corresponds to an internal portion of the Ac element and cannot therefore hybridize to the Ds elements which are too deleted compared to Ac and no longer have this portion of Ac. The hybridization is therefore limited to the transposable elements and/or to the sequences exhibiting good homology with the Ac element. This probe originates from a plasmid which contains the autonomous element Ac9 initially inserted into the p locus of maize. The 1605 bp fragments were extracted from the agarose gel after digestion and migration. They were then purified before being hybridized on the nylon membranes.

Only bands greater than 8 kb in size are present at the top of each lane for the DNA samples from A188 and from an elite line digested with PvuII and BglII/PvuII; no band close to 2.5 kb in size is visible. This digestion profile shows that the genomic DNA was partially digested with PvuII. The absence of this 2524 bp band in the A188 plants may be due to a methylation state of the Ac transposases, which would therefore be inactive, or else to the absence of a complete copy of an Ac element in these genetic backgrounds.

In addition, the A188 line contains all the necessary constitutive genes (A1, A2, Bz1, Bz2, C2) and the recessive alleles of the genes which regulate the anthocyan synthetic pathway (r-r,C1,p1). It does not therefore express any pigment of the anthocyan type, except in the anthers of the leaf sheath, which can sometimes be red. It is therefore an advantageous recipient line for expression of the anthocyan marker after crossing.

b) Transformation with *Agrobacterium* and Regeneration

The transformation technique used is that described by Ishida et al., 1996. *Agrobacterium tumefaciens* was employed, in particular using immature embryos of 10 days post-fertilization. All the media used are given in the reference cited. The transformation begins with a coculturing phase in which the immature embryos of the maize plants are brought into contact for at least 5 days with a strain of *Agrobacterium tumefaciens*, such as LBA 4404 (Ooms et al., 1981), or another one, EHA 101 (Hood et al., 1986), EHA105 (Hood et al., 1993) or AGL1 (Lazo et al., 1991), containing superbinary vectors. The superbinary plasmid is the result of a homologous recombination between an intermediate vector carrying the T-DNA containing the gene of interest and/or the selection marker derived from the plasmids described in the preceding examples, and the vector pSB1 from Japan Tobacco (EP 672 752) which contains: the virB and virG genes of the plasmid pTiBo542 present in the supervirulent strain A281 of *Agrobacterium tumefaciens* (ATCC 37349) and a homologous region found in the intermediate vector allowing this homologous recombination. The embryos are then placed on LSA medium for 3 days in the dark and at 25° C. A first selection is carried out on the transformed calluses: the embryogenic calluses are transferred onto LSD5 medium containing 5 mg/l of phosphinotricine and 250 mg/l of cefotaxime (elimination or limitation of the contamination with *Agrobacterium tumefaciens*). This step is carried out for 2 weeks in the dark and at 25° C. The second selection step is carried out by transferring the embryos which have developed on LSD5 medium onto LSD10 medium (10 mg/l phosphinotricine) in the presence of cefotaxime, for 3 weeks under the same conditions as above. The third selection step consists in excising the type I calluses (fragments of 1 to 2 mm) and in transferring them for 3 weeks in the dark and at 25° C. onto LSD10 medium in the presence of cefotaxime.

The regeneration of the plantlets is carried out by excising the type I calluses which have proliferated and transferring them onto LSZ medium in the presence of 5 mg/l phosphinotricine and cefotaxime for 2 weeks at 22° C. and under continuous light.

The plantlets which have regenerated are transferred onto RM+G2 medium containing 100 mg/l cefotaxime for 2 weeks at 22° C. and under continuous illumination for the development step. The plants obtained are then transferred into a phytotron for the purpose of acclimatizing them under glass.

1.3 Selection of Resistant Transformants and Molecular Analysis a) Selection on Selective Medium (1) Selection of Transformation Events Resistant to Glufosinate (Ds::bar)

Several selective media, the medium for initiation of calluses, maturation and regeneration, make it possible to effectively eliminate the nontransformed events sensitive to the selective agent. Only the transformed calluses are regenerated and can produce plantlets. In order to eliminate the plantlets which may have escaped the selections, and which have developed in the vicinity of resistant plants (the bar gene produces a protein which enables the plant to detoxify glufosinate), a leaf painting assay is carried out on part of a leaf of the plant at the six-leaf stage, with a solution containing glufosinate (0.5% (v/v) Basta). The sensitive leaf exhibits a characteristic drying out one week later.

(2) Selection of the Transformation Events Resistant to Kanamycin (Ds::nptII)

Selection of the transformation events was carried out on media containing various concentrations of kanamycin or of geneticin.

A test for detecting the transformed plants in a greenhouse was also set up. A few drops of a solution of kanamycin (500 mg/l) and Tween 20 (0.1% (w/v)) are deposited into the comet formed by the leaves of the young plants (three-leaf stage, approximately two to three weeks). The leaves of the sensitive plants exhibit, as they grow, bleached sectors at the site where they were in contact with the solution. This test is nondestructive and makes it possible to recover the sensitive plants.

b) Molecular Analysis

The regenerated plants are analyzed by PCR and by Southern blotting in order to eliminate those which have escaped selection and to identify the single-copy transformation events which will preferably be used in this invention. These plants which have integrated the T-DNA into their genome are the TO primary transformants. The analytical technique used is derived from that described by Southern (1976).

(1) Identification by PCR

PCRs were carried out on the DNA extracted from these plants, in order to verify that the plants resistant to the selective agents had indeed integrated the T-DNA into their genome, and that there has not been any transposition of Ds::M The pair of oligonucleotides EM13-EM14 (SEQ ID NO:1-SEQ ID NO:2) amplifies a fragment the size of which is 280 bp when the Ds::M has been excised from the T-DNA, and no fragment if the Ds::M is still inserted into its initial site on the T-DNA.

The pair of oligonucleotides Actint1-Actint2 (SEQ ID NO:3-SEQ ID NO:4) amplifies a fragment of the actin intron present in the Ds::MS, the size of which is 480 bp.

The transformation events selected on selective medium which are positive by PCR with the Actint1-Actint2 pair and negative by PCR with the EM13-EM14 pair have therefore integrated into their genome at least part of the T-DNA containing the Ds::M element which has remained in its initial insertion site.

(2) Determination of the Number of Copies of the T-DNA

Molecular analyses were carried out on the DNA extracted from leaves of the selected plants in order to determine the single-copy transformation events.

The DNA of the plants positive for Ds::bar was digested with the EcoRV endonuclease, which cleaves only once in the T-DNA, between the bar open reading frame and the actin intron.

The DNA of the positive plants was digested with the NcoI endonuclease, which cleaves only once in the transfer DNA, within the npt II open reading frame.

After electrophoresis, transfers were carried out and the resulting membranes were hybridized successively with the following probes:

for the Ds::bar plants, Bar (Bar gene digested with SmaI, called S006), actin intron (called S063) and 5'Nos (called S064) probes;

for the Ds::nptII plants, npt II (called S020), actin intron (called S063) and 5'Nos (called S064) probes; and for the actin intron, 5'Nos and nptII probes are defined by PCR using oligonucleotides chosen according to methods known to those skilled in the art (cf. attached table).

The Bar, npt II and actin intron probes make it possible to estimate the number of copies of transfer DNA inserted into the genome. The 5'Nos probe makes it possible to demonstrate a potential excision of the Ds element from the T-DNA. These three probes therefore make it possible to determine the plants which have a single copy of the complete transfer DNA.

For Ds::bar, when there has been only a single insertion of the T-DNA, one fragment is revealed for each of the three probes. Furthermore, if the Ds is not excised, the size of the DNA fragments revealed by the two probes Bar and 5'Nos is the same.

For Ds::nptII, when there has been only a single insertion of the T-DNA, one fragment is revealed for the 5'Nos and actin intron probes, and two fragments are revealed with the nptII probe. Furthermore, if the Ds is not excised, one of these two fragments is also revealed with the 5'Nos probe and the other with the actin intron probe.

According to the invention, the plants chosen for the crosses with the source of transposase are preferably the plants derived from the single-copy transformation events.

Example 2

Crossing with an R-nj::Ac Line which Has the Ac Transposase Inserted Into a Phenotypic Marker Gene 2.1. Source of Transposase R-nj::Ac The W22/R-nj::Ac line contains the constitutive genes C2, A1 and A2 and the regulatory genes C1, p1 and B-b. This line therefore carries all the factors required for the violet pigmentation in the aleurone (identified as normal). This line also possesses the unstable allele R-nj::Ac created by chromosome translocation by Dellaporta et al. in 1988).

This line homozygous for the R-nj::Ac allele is used here and is derived from seeds originating from the Stock Center and is called As. The seeds exhibit reasonably large colored sectors corresponding to the cells in which the Ac has become excised from the R-nj allele.

Molecular analyses were carried out on the DNA extracted from leaves of As plants homozygous for the R-nj::Ac allele, in order to evaluate the activity of the Ac element inserted into the R-nj gene. This study of the methylation state of the Acs present in the As lines was carried out as for the A188 lines and the elite lines which are used for the transformation and for the introgression of the genes of interest. Many bands greater than 8 kb in size are present at the top of each lane of all the samples. They correspond to undigested or partially digested DNA. However, the presence of a 2.5 kb band derived from the digestion with PvuII, a methylation-sensitive enzyme, indicates that at least one copy of the Ac element is nonmethylated in the genome of this As line.

2.2. Introgression of the R-nj::Ac Allele Into Other Lines

The R-nj::Ac element can advantageously be introgressed into lines known to be favorable to callus regeneration, such as the A188 line (Walbot et al., 1994) or the Hill line. The R-nj::Ac element can also be introgressed into elite lines, used for the introgression of the genes of interest.

To verify the activity of the Ac element over the generations, a phenotypic analysis was carried out on the seeds of the ears derived from these crosses. The ears obtained with these crosses exhibit variegated seeds.

The results of the crosses between the As line and the elite lines, or A188 and M1, show that the R-nj gene can be expressed in other genetic backgrounds, either by virtue of the presence of the constitutive genes required for the expression of the phenotype in these lines (as is the case for A188), or because they are introduced into the cell by the As line.

The variegation observed on the seeds suggests that the Ac is still active in this generation since it transposes out of the R-nj allele in certain parts of the seeds derived from these crosses.

Multiple introgressions carried out in the A188 and Hill lines and in an elite line (up to 3 crosses in the line, which corresponds to approximately 93% of A188 and 7% of W22) made it possible to confirm these results. Lines homozygous for the R-nj::Ac allele were therefore produced by self-pollinations.

2.3. Crosses

The pollination is carried out manually by a technique known to those skilled in the art, by depositing the pollen from the source of transposase As onto the bristles of the transformants, preferably in the direction of male plant possessing the transposase into female plant containing the Ds::M element.

A part of the ear is sometimes removed in order to extract therefrom immature embryos intended for cell biology protocols such as embryo recovery or callogenesis. The cut section is preferably covered with a fungicide in order to avoid rot and bacteria.

The embryos taken 10 to 15 days after pollination are placed, rounded part facing upward, on 25 ml of regenerating medium RM+ (Ishida et al, 1996; Negrotto et al., 2000). The dishes are then placed in a culture chamber with a regulated photoperiod (16 h day-8 h night) and at constant temperature (23° C.). The plantlets are then acclimatized in a phytotron after 10 to 15 days of having been placed in culture, and before being transferred into a greenhouse.

Example 3

Selection of the Events Exhibiting an Excision of the Ds::MS Element

The molecular studies, described in example 1.3, made it possible to identify a single-copy Ds::nptII transformation event and a single-copy Ds::bar event preferably used to evaluate a potential excision. These studies also showed that the Ds::M element is stable in the A188 line (study carried out on T0 primary transformants and T1 first descendants by PCR and Southern blotting).

The phenotypic and molecular studies of the As line, described in example 2), made it possible to show that there was, in their genome, (at least) one copy of the active Ac element capable of becoming excised out of the R-nj allele in the initial genetic background of the W22 line or in the background of another line.

The phenotypic analysis of the variegation of the R-nj allele on the F1 ears derived from the As X Ds::M crosses confirmed that the Ac element was still active in this generation: the presence of anthocyan sectors on all the mature seeds shows that there has been production of transposase and somatic excision of the Ac out of its initial insertion site. The introduction, by crossing, of a new Ds element into the cell in no way changed the ability to follow the activity of the source of transposase.

It is considered that the Ds element is not genetically linked to the R-nj::Ac allele.

It therefore remains to be determined whether the transposase expressed by the Ac element inserted into the R-nj allele can allow excision of the Ds::bar and Ds::nptII elements.

3.1. Using F1 Plants (Conventional Pathway)

Crosses were undertaken after establishment of the single-copy lines in order to verify whether the Ds::bar and Ds::nptII elements are capable of transposing in planta.

The plants which were sources of transposase were used as pollinators (due to a female semi-sterility in these plants).

a) Search by PCR of Somatic Excision on F1 Plants Resistant to the Selection Agent Some of the F1 descendants derived from the crosses between the Ds::MS plants and the As plants were sown and the DNA was isolated from young leaves from each F1 plant thus generated. Since one of the parents is hemizygous for the T-DNA and the other is homozygous for the R-nj::Ac allele, it is expected that the two components Ac and Ds will be transmitted to 50% of the F1 plants derived from these crosses.

In order to identify the F1 plants having the T-DNA and to detect possible somatic excisions, tests for resistance to the selective marker were carried out on the young plants in parallel with sequence amplification tests on the DNA from leaves.

(1) Ds::nptII Plants

From 3 to 5 ml of a solution of 500 mg/l kanamycin sulfate +0.1% tween are placed in the cornet formed by the leaves of the plant. The sensitive plants develop chlorotic sectors on the parts of the leaves which were in contact with the solution.

(2) Ds::bar Plants

Leaf painting is carried out by painting a leaf with a solution of glufosinate ammonium.

A first selection of resistance to the antibiotic or to the herbicide, by virtue of a nondestructive application, made it possible to determine which plants had the selection marker gene.

When a Ds element excises after production of transposase, an empty donor site remains. PCR amplification with the oligonucleotides EM13 (SEQ ID NO:1) and EM14 (SEQ ID NO:2) makes it possible to synthesize a specific fragment of 280 bp when the Ds::bar or Ds::nptII element has been deleted from the T-DNA. A series of amplifications was therefore carried out with the EM13-EM14 pair on DNA extracted from the plants derived from the Ds::nptII X Ac cross in order to detect a possible somatic excision in certain cells of the samples of leaves taken.

The PCR analysis of these F1 plants showed that somatic excision was present for all the F1 plants which had inherited the T-DNA and the R-nj::Ac allele. No amplification was detected on the plants having only the T-DNA, or on the plants having neither of the two components.

In addition, all the plants for which a somatic excision was detected proved to be resistant overall to the antibiotic.

This band therefore indicates the presence of a somatic excision in certain cells of the individuals carrying the T-DNA and the R-nj::Ac allele. In accordance with what was predicted, no event of germinal excision of the Ds::M element occurred for these plants, the two components having been grouped together in the same cell for too few cell generations (from pollination to the young plant).

The transposition would have had to have taken place in the gametes in order to hope to observe a germinal excision, or in the gamete mother cells, which increases the weak gamete excision possibility; it would therefore have been surprising to obtain germinal excision as soon as the F1 generation.

However, in the strategy envisioned, it is the frequency of germinal excision which is preferable for eliminating the marker gene:

a somatic excision does not generally affect the gametes and leads to the formation of chimeric seeds and individuals in which most of the cells still have the excision marker, a germinal excision affects the cells which will differentiate in the gametogenesis pathway, and leads to the formation of seeds and individuals consisting of cells in which the Ds has been excised (and may be reinserted) and which no longer have the selection marker gene.

b) Search by PCR for Potential Germinal Excisions of the Marker Gene Among the Sensitive Plants For this reason, the search for a germinal excision was carried out on the F2 generation. The amplification bands specific for the excision were assayed for each F1 plant, this assay making it possible to reflect, through the somatic excision rate, the activity of the source of transposase.

The F1 plants exhibiting most somatic excision were crossed with plants of the A188 line or with plants of an elite line. These crosses were carried out in both directions, the plants possessing the two components Ac/Ds::M having been used as females and/or as males in order to increase the possibilities of germinal excision by an F1 plant. The seeds thus formed were brought to maturation. Batches of F2 seeds originating from Ds::nptII X Ac F1 plants resistant to kanamycin and from Ds::bar X Ac F1 plants resistant to glufosinate, and derived from various crosses, were sown. No phenotypic examination relating to the variegation was carried out here. The seeds expressing the phenotype or the nonpigmented seeds are chosen for the sowing with the same probability, in order to avoid any bias.

A simple way to test the frequency of germinal excision in this system is to select the F2 plants for their sensitivity to the selective agent and to test them by molecular analyses. Ds::bar F2 plants and Ds::nptII F2 plants were thus tested for PCR amplification of the 280 bp excision-specific band.

An F2 plant is sensitive to the selective agent either via segregation, and consequently the 280 bp band should not be amplified, or by germinal excision of the marker gene, and in this case, the excision-specific band is detectable by PCR. This study made it possible to amplify the excision-specific band from the DNA of F2 plants derived from the crosses:

Ds::bar/Ac X A188;

Ds::bar/Ac X elite line;

elite line X Ds::nptII/Ac; and

Ds::nptII/Ac X elite line.

Southern hybridizations and also PCR analyses were carried out on these selected plants and also on the initial T1 Ds::bar and T0 Ds::nptII plants, and the results obtained are as follows.

The PCR and Southern analyses show that the selected F2 plants inherited part of the T-DNA containing the left border, the sequences of interest, the scar left by the excision of the Ds and the right border; the Ds::M element was not genetically transmitted to the F2 plants as it was for the F1 plants. These F2 plants are therefore plants derived from events of germinal excision of the Ds::M element out of the T-DNA.

Overall frequencies of germinal excision are variable from one F2 lineage to another and are quite low. As regards the Ds::bar construct, on the plants having inherited the T-DNA, only a few plants no longer have the Ds::bar element, which gives a frequency of germinal excision of 0.4%. The frequency of germinal excision of the Ds::nptII element is slightly higher and reaches 0.7%.

This frequency of germinal excision is relatively low. The phenomenon of floral transition is more rare in maize than in tomato or garden arabis: in maize, there are only two or three meristems per individual which differentiate into sex organs and form the gametes: one for the panicle (male organ) and one or two for the ears (female organs). The germinal excision must therefore affect either one of these meristems before gametogenesis, or a gamete.

c) Segregation of the T-DNA and of the R-nj::Ac Allele

Once the F2 plant carrying the T-DNA without the selection marker gene has been characterized, segregation of the transposase inserted into R-nj and of the T-DNA can be performed. This segregation may take place during the introgression of the T-DNA into the elite line. It is sufficient to select the plants which carry the T-DNA but which do not express any anthocyan pigment of the navajo type. This segregation can also be followed by molecular analyses of the Southern type using the Sac and S064 probes.

3.2. Method of Selection on Calluses for the Ds::nptII X As F1 Embryos

In order to increase the frequency of germinal excision, a callogenesis step was carried out on immature F1 embryos having both components, i.e. the Ds::nptII element inserted into the T-DNA and the source of transposase Ac inserted into the R-nj allele. The line chosen as source of transposase is here a homozygous source derived from the first introgression of W22/R-nj::Ac into A188. The callus therefore has approximately 75% of the A188 genome and 25% of the W22 genome. A188 is a line which makes it possible to obtain type II calluses.

During the growth of the callus, and using a cell having experienced a somatic excision event, it is possible to generate an embryogenic callus sector consisting of a mass of somaclonal cells no longer having the selection marker gene. Phenotypic or molecular identification of this sector would make it possible to regenerate an individual free of a marker gene from these cells with a frequency higher than via the conventional route.

a) Initiation of Calluses from Immature F1 Embryos on Selective Medium and Selection of Resistant Calluses F1 embryos derived from crosses between the Ds::M transgenic plants and the sources of transposase homozygous for the R-nj::Ac allele were taken from ten to twelve days after pollination, placed sterilely on an N6 medium and cultured in a dark room in order to initiate the formation of undifferentiated type II calluses according to the method of Armstrong et al., 1985.

After having removed the germinating stems after 15 days of initiation, the calluses are kept in the dark at 25° C. throughout the duration of callus induction and the first part of multiplication. The calluses start to become visible one week after initiation. At each subculturing, i.e. every two or three weeks, the white, embryogenic and friable parts are selected and separated from the more compact or mucosal parts.

After 2 to 3 weeks of initiation, the calluses formed are duplicated in two parts:
one half is placed on a nonselective N6 medium in order to continue the callus multiplication;
the other half is placed on an N6 medium containing 50 mg/l kanamycin, in order to identify the resistant calluses carrying the T-DNA.

The selection of calluses with kanamycin requires a step under light, in a culture chamber. The antibiotic in fact inhibits peptide synthesis in the mitochondria and the chloroplasts. The inhibition is based on the similarity between protein synthesis in these organelles and bacterial protein synthesis. Plant cells are therefore generally intolerant to aminoglycosides such as kanamycin or gentamycin. However, for a relatively low dose, kanamycin is not destructive and allows selection by colorimetric phenotype: the resistant calluses which have the nptII gene go green when they are exposed to light (the functional chloroplasts accumulate chlorophyll), whereas the sensitive calluses remain yellow.

This selection step makes it possible to identify the calluses which have the T-DNA and the Ds::nptII element and to eliminate the calluses which possess only the R-nj::Ac component in their genome (in the case of a homozygous source of transposase).

b) Multiplication of the Resistant Calluses on the Nonselective Medium

The parts of the resistant calluses which were duplicated and placed on nonselective medium are grown in the dark. There is therefore multiplication of the cells which have the two components. During this multiplication, there will be production of transposase and a certain number of cells will be derived from events of excision of the Ds::nptII element out of the T-DNA. These cells, in multiplying, will lead to the formation of chimeric calluses consisting of sectors of somatic excision of Ds::nptII and sectors free of excision.

The calluses are then placed under light for one week. The yellow parts are roughly isolated.

c) Regeneration of Plantlets From an Excision Sector

The ends of isolated calluses are regenerated on a nonselective medium in a culture chamber and under light. Plants are thus regenerated from the various embryogenic parts and potentially from a sector where there is excision of the Ds::nptII element.

d) Search for Germinal Excision on the Sensitive Plants

When the plants have reached the three-leaf stage, they are treated with a kanamycin sulfate solution. The plants exhibiting chlorotic sectors are therefore plants sensitive to the selective agent which are derived from an initially resistant callus. Among the plants tested, certain plants originating from the same embryo proved to be sensitive to kanamycin.

PCR and Southern analyses in fact showed that the Ds::nptII element had been excised from its initial position and had not become reinserted. The frequency of excision is therefore considerably increased by virtue of culturing calluses and reaches 8% of the plants thus regenerated.

Sequencing of the scars left on the T-DNA by the excision of the Ds::nptII element was carried out for the plants generated via the reproductive pathway and via the vegetative pathway. Analysis of the sequences obtained shows that some plants of the reproductive pathway are derived from two different germinal excision events although they are derived from the same cross. On the other hand, the sequences of the scars for the plants obtained by callogenesis are identical. This would confirm that these plants are derived from the same excision event.

3.3. Improved Method for Selecting Germinal Excision Events in the F1 Generation According to a preferred embodiment of the invention, the expression cassette comprising a nucleotide sequence encoding a selection marker (ii) also comprises, within the Ds element, another phenotypic marker gene of the nondestructive reporter gene type. This reporter gene may, for example, be the gene encoding a green fluorescent protein, GFP (Nielsen et al., 1999), detection of the expression of which in the tissues is not destructive: the observation is carried out under a magnifying lens equipped with a light of specific wavelength. When the Ds element is excised, the GFP gene is no longer present and the sectors of somatic excision can be detected under the "GFP magnifying lens" since they no longer fluoresce.

In the context of this example, the plasmid pBios491 is derived from the plasmid pBios340 (Ds::nptII) described in example 1a, by insertion, into the Ds element and in the same reading frame as the NptII cassette, of an expression cassette containing the CsVMV promoter of the Cassaya vein mosaic virus (WO 97/48819), the first intron of the rice actin 1 gene, the GFP open reading frame (Nielsen et al., 1999) and the Nos terminator.

Ds::GFP-nptII is 5473 bp in Size (FIG. No. 5).

As described in examples 3.1 and 3.2, selection of the germinal excision events may follow the steps below:

the T1 embryos derived from the cross between the transformants carrying the gene of interest-Ds::MS cassette and the source of transposase are recovered 10 days after pollination;

these embryos are removed and are placed in culture on a nonselective callogenesis medium in the dark for 15 to 30 days; and the calluses are then observed under the GFP magnifying lens and the nonfluorescent fraction of the callus, corresponding to the sectors of somatic excision, is then removed for multiplication and regeneration of the plant. The plants thus produced contain the gene of interest free of foreign ancillary sequence.

There are therefore many advantages to this vector Ds::GFP-MS in the context of the invention, specifically:

identification of the immature F1 embryos carrying the transgene, which fluoresce, is carried out by simple visual observation under the GFP magnifying lens;

callogenesis from the selected embryos can be carried out on a nonselective medium in order to induce many callus initiations and thus promote the initiation of somatic excision zones lacking the selection gene;

selection of the calluses derived from cells in which there has been somatic excision is facilitated under the fluorescence magnifying lens; in addition, these calluses can be directly and precisely removed in order to be regenerated;

once the plants have been regenerated, the absence of fluorescence (somatic excision) can also be confirmed.

Example 4

Production of Male Sterile Plants Lacking the Kanamycin Marker Gene 4.1. Preparation of the Constructs A9-barnase-Ds::nptII The plasmid pBios424 is derived from the plasmid pBios340 described in example 1a by insertion of the 'gene of interest' cassette comprising the A9 promoter (WO 92/11379), corresponding to the 5' noncoding region of the *Arabidopsis thaliana* A9 gene, the barnase gene open reading frame (Hartley, 1988; Gene Bank No. X 12871) and the 3' CaMV terminator (Franck et al. 1980; Gene Bank No. V 00141), outside the Ds element. The barnase gene, which confers male sterility, encodes a ribonuclease (RNase). This gene was isolated from Bacillus amyloliquefasciens and is described in the publication by Hartley (1988).

Figure 6:
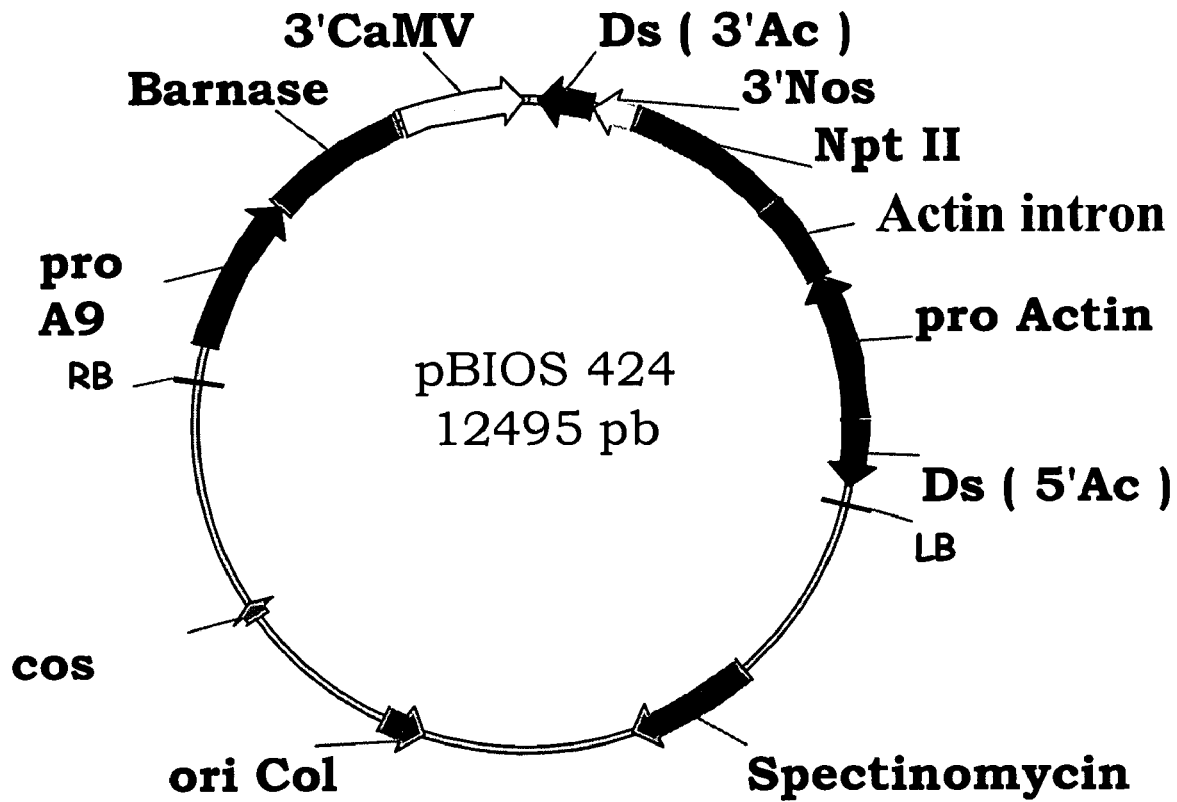
FIG. 6: restriction map of the plasmid pBios424 comprising the A9 promoter-barnase-CaMV 3' terminator and the NptII gene for kanamycin resistance in a Ds-dissociating element.

A9-barnase-Ds::nptII is 12495 bp in size (FIG. 6).

The superbinary plasmid pRec424 used for the transformation is obtained by homologous recombination between an intermediate vector derived from the plasmid pBios424 and the vector pSB1 from Japan Tobacco (EP 672 752), as described in example 1b.

4.2. Selection of the Resistant Transformants and Molecular Analysis 7 transformation events were produced, 5 of which were selected as being male sterile (A9-barnase) and resistant to kanamycin (NptII).

Molecular analysis of these events was carried out in order to determine the single insertions. This analysis makes it possible to characterize the transformation events selected in terms of number of copies of the T-DNA integrated and of the number of integration loci involved. For this, various molecular probes are used.

The genomic DNA of the plants was digested with the NcoI restriction enzyme, separated by agarose gel electrophoresis and transferred onto a nylon membrane (Hybond N+ membranes) for the purpose of hybridization with the various molecular probes.

Choice of Molecular Probes:

Use of the A9 promoter (S007, SEQ ID NO:7), barnase (S032, SEQ ID NO:8), and actin intron probes, coupled with the NcoI enzyme restriction, makes it possible to characterize the molecular profile of the transformation events.

Since the sequence of the basic plasmid was known, pairs of oligonucleotides specific for the plasmid regions located outside the T-DNA were synthesized and then used as primers to generate by PCR an extra-right border (RB) probe and an extra-left border (LB) probe. On the right side, 40 base pairs from the right border, the PCR amplification generated a 353 base pair probe and on the left side, 29 base pairs from the left border, the amplification generated a 299 base pair probe. The probe referred to as "extra-border probe" consists of a mixture of the two probes described above. Its use makes it possible to detect the plants exhibiting no integration of plasmid regions close to the T-DNA.

The size of the signals expected after hybridization with the various probes for a single untruncated T-DNA insertion, and when the borders have not been exceeded, is as follows:

| Restriction enzyme | Number of copies | Size of expected signals | | | |
|---|---|---|---|---|---|
| | | A9 promoter (pro A9) probe | Actin intron probe | Barnase probe | Extra-border probe |
| NcoI | 1 | ≧1189 bp | ≧2550 bp | 2733 bp | No signal |

The results of the signals observed on the primary transformants show that the 5 events exhibit single insertion profiles (1 or 2 copies).

4.3. Crossing With an R-nj::Ac Line and Selection of the Events Exhibiting an Excision of the Ds::MS Element The primary transformants exhibiting single insertion profiles were crossed with the source of transposase homozygous for the Rnj-Ac allele as described in example 2.

The embryos corresponding to the T1 (or F1) generation were removed 15 days after pollination, and cultured in vitro on culture medium containing 50 mg of kanamycin.

PCR analysis with suitable oligonucleotides may make it possible to verify whether these somatic excision events have taken place in the selected T1s.

The DNA samples from the T0 and T1 plants were subjected to PCR amplification using the Barn5 (SEQ ID NO:6) and EM11 (SEQ ID NO:5) oligonucleotides. If the Ds::nptII is excised from the T-DNA, a 760 bp fragment can be amplified. If it is not excised, the 4160 bp fragment which should be amplified does not appear under the PCR conditions.

The 760 bp amplification band revealing excision of the Ds::nptII is present in most of the samples of T1 plants but not in the T0s. No somatic excision was revealed in the T0s, which demonstrates that the excision is correctly controlled.

The electrophoresis gel was transferred onto a nylon membrane so as to be hybridized with a 3'CaMV probe in order to confirm the identity of the amplified fragment.

The PCR experiments therefore clearly made it possible to confirm the presence of somatic excision in most of the T1 plants carrying the 2 constituents: Ds::nptII and transposase.

After coming out of in vitro, the T1 plants are acclimatized in the phytotron and then in a greenhouse. At flowering, the selected T1 plants are crossed with an elite line, defined as being a line having a considerable agronomic and commercial potential, at a given period of time. According to the method of the invention, germinal excision events can be found by screening a large number of F2 plants derived from these T1 lines.

Primers used to detect excision of the Ds::Bar and Ds::npt II elements

| Name | SEQ ID NO | Sequences |
| --- | --- | --- |
| EM13 | 1 | 5'-CGACAATCTGATCATGAGCG-3' |
| EM14 | 2 | 5-CTTAATAACACATTGCGGACG-3' |
| Barn5 | 6 | 5'-GGTTTCGCTCATGTGTTGAGC-3' |
| EM11 | 5 | 5'-CATTGCGGACGTTTTTAATGTACTG-3' |

Primers used to detect the Ds::npt II transformants

| Name | SEQ ID NO | Sequences |
| --- | --- | --- |
| Actint1 | 3 | 5'-CGAATTCGCGCCGGTAAC-3' |
| Actint2 | 4 | 5'-TCGTGCCGAATTCGATATCAAGC-3' |

The probes used for the Southern blots are given below

| Name | Methods of production | Target sequence | Size |
| --- | --- | --- | --- |
| S006 | Restriction fragment: SmaI-SmaI | Bar gene | 600 bp |
| S063 | PCR fragment: pair of oligonucleotides Actint1-Actint2 | Actin intron | 480 bp |
| S064 | PCR fragment: pair of oligonucleotides 5'Nos1-5'Nos2 | 5'pNos | 130 bp |
| S020 | PCR fragment: pair of oligonucleotides kana7-kana8 | npt II gene | 1000 bp |
| SAc | Restriction fragment: HindIII—HindIII | Ac gene | 1605 bp |
| S007 | Restriction fragment: HindIII—HindIII | Barnase | 900 bp |
| S032 | Restriction fragment: XbaI/XhoI | A9 promoter | 1000 bp |

DOCUMENTS CITED

All sequences, patents, patent applications or other published documents cited anywhere in this specification are herein incorporated in their entirety by reference to the same extent as if each individual sequence, publication, patent, or patent application was specifically and individually indicated to be incorporated by reference.

An et al. (1986), Plant Physiol., 81: 86-91
Anderson O. D. et al. (1989), T.A.G., 77:689-700
Armstrong et al. (1996), Planta, 164:207-214
Bechtold et al. (1993), Comptes rendus Académie des Sciences Paris, Series 3,316:1194-1199
Bevan et al. (1983), VAR II:369-379
Brink et al. (1973), Genetics, 73:273-296
Chalfie et al. (1994), Science, 263:802-807
Chesson A. et al. (2000), La Recherche, 327:27-44
Chopra S. et al. (1999), PNAS, USA 96:15330-15335
Chernyshev et al. (1988), Genetika, 24:1338-1344
Chupeau et al. (1989), Biotechnology, 7(5):503-508
Dellaporta S. et al. (1988), Plenum Press, pp 263-282
Depicker et al. (1982), Mol. Appl. Genet. 1: 561-573
Depigny-This et al. (1992), Plant Mol. Biol., 20:467-479
Fedoroff N. V. et al. (1983), Cell, 35:243-251
Finer et al. (1992). Plant Cell Report, 11:323-328
Flavell R. B. et al. (1992), Bio/Technology, 10: 141-144
Franck et al. (1980) Cell, 21, 285-294
Fromm M. et al. (1990), Biotechnology, 8:833-839
Grotewold E. et al. (1998), Plant Cell, 10:74-740
Guerche et al. (1987), Mol. Gen. Genet., 206:382
Hartley, R. W (1988) J. Mol. Biol. 202, 913-915
Herrera-Estrella et al (1983), EMBO J. 2, 987-995
Hood E. E. et al. (1986), Journal of Bacteriology, 168: 1291-1301
Hood E. E. et al. (1993), Trans. Res., 2:208-218
Ishida et al. (1996), Nature Biotechnology, 14: 754-750
Jefferson et al. (1987), Plant Mol. Biol., 5:387-405
Kay et al. (1987), Science, 236:4805
Lazo G. R. et al. (1991), Biotechnology (NY), 9(10):963-967
Lechelt et al. (1989), Mol. Gen. Genest, 219:225-234
Ludwig S. et al. (1989), PNAS of USA, 86:7092-7096
Lyzrik L. et al. (1997), Nucleic Acids Research, 44:123-132
MacRae A. et al. (1994), Genetica, 92 (2): 77-89
Mannimem I. et al. (1993), Plant Mol Biol, 22:829-846
Mc Elroy et al. (1991), Mol. Gen. Genet., 231:150-160
Mototashi R. et al. (1996), Mol Gen Genet, 25:148-152
Müller-Neumann et al. (1984), Mol Gen Genet, 228:201-208
Negrotto D. et al. (2000), Plant cell Rep., 19:798-803
Neuhaus et al. (1987), Theoretical and applied Genet., 75(1):30-36
Nielsen K. et al. (1999) Physiological and Molecular Plant Pathology, 54, 1-12
Ooms G. et al. (1982), Plant Molecular Biology, 1:265-271
Pereira et al. (1986), EMBO, J5:835-841
Roberts et al. (1989), Plant Cell, 1: 569-578
Schocher et al. (1986). Biotechnology, 4:1093-1096
Seth J. Davis (1998), Plant Molecular Biology, 36: 521-528.
Yoder J. T. et al. (1993), Bio/Technology, 12:263-266
Walbot V. et Bodeau et al. (1994), Maize News Letter, 68: 98-99
Watson et al. (1994), Publisher De Boeck University, pp 273-292
Weising K. et al. (1995), CRC Press, Boca Raton. FL.
White et al. (1990), NAR 18:1062.

We claim:

1. A method for obtaining a transgenic maize plant containing a coding sequence of interest that is free of ancillary selection marker sequence comprising:
    (a) transforming a maize plant, or a cell of a maize plant, that lacks an active Ac element transposase, with a transformation vector comprising:
       (1) a first expression cassette comprising a coding sequence of interest that is not bordered by mobilizable sequences of a maize active Ac element transposon; and
       (2) a second expression cassette comprising a nucleotide sequence encoding an ancillary selection marker that is bordered by the mobilizable sequences of a maize active Ac element transposon, wherein said nucleotide sequence encoding the ancillary selection marker is operably linked to a plant expression control sequence,
    to obtain primary transformants;
    (b) growing the primary transformants under selective conditions to obtain at least one transformed parental maize plant having the ancillary selection marker coding sequence;
    (c) producing an F1 generation by crossing the selected transformed parental maize plant with a second parental maize plant, said second maize plant having within its genome a sequence encoding an endogenous active Ac element transposase that operates on the mobilizable sequences of the second expression cassette, wherein said sequence encoding the endogenous active transposase encodes the active Ac element within an R-nj::AC allele of the R-nj chromosomal locus such that excision of the said Ac element results in the production of anthocyanin-containing sectors on the crown of the seed, including the embryo;
    (d) selecting a maize plant from the F1 generation having said anthocyanin-containing sectors; and
    (e) regenerating a maize plant from the plant, or a cell of the maize plant, selected in (d),
    such that a transgenic maize plant containing a coding sequence of interest that is free of ancillary selection marker sequence is produced.

2. The method of claim 1, wherein the ancillary selection marker coding sequence is selected from the group consisting of an antibiotic resistance coding sequence, a herbicide resistance coding sequence, a colorimetric marker coding sequence and a luminescent marker coding sequence.

3. The method of claim 1, wherein the ancillary selection marker coding sequence is selected from the group consisting of an nptII coding sequence and a bar coding sequence.

4. The method of claim 1, wherein the second expression cassette further comprises a nucleotide sequence encoding a reporter protein, wherein expression of the reporter protein is detectable without destruction of the primary transformants.

5. The method of claim 4, wherein the reporter protein is a green fluorescent protein.

6. The method of claim 1, wherein the transgenic maize plant belongs to the A188 line.

7. The method of claim 1, wherein the second parental maize plant of step (c) is selected from the group consisting of A188 and W22 lines homozygous for said R-nj::Ac allele.

8. The method of claim 1, wherein the selection of the maize plant in step (d) comprises: producing calluses from immature F1 embryos obtained from the F1 generation, visually selecting the calluses containing the ancillary selection marker, multiplying calluses and selecting sectors of excision of the ancillary selection marker coding sequence.

9. The method as claimed in claim 8, wherein regenerating maize plants from the maize plant, or cell from the maize plant, selected in (d) comprises culturing selected calluses of immature embryos of F1 generation under conditions that allow regeneration of maize plants.

* * * * *